United States Patent [19]
Okada et al.

[11] Patent Number: 5,977,389
[45] Date of Patent: Nov. 2, 1999

[54] NAPHTHOQUINONE DERIVATIVE

[75] Inventors: Hideki Okada; Nobuko Akiba; Fumio Sugai, all of Osaka, Japan

[73] Assignee: Mita Industrial Co., Ltd., Osaka, Japan

[21] Appl. No.: 09/033,895

[22] Filed: Mar. 3, 1998

[30] Foreign Application Priority Data

Mar. 6, 1997 [JP] Japan .................................. 9-052040

[51] Int. Cl.⁶ .................................................. C07C 50/12
[52] U.S. Cl. .......................................... 552/299; 552/296
[58] Field of Search .................................. 552/296, 299; 560/51

[56] References Cited

FOREIGN PATENT DOCUMENTS

| | | |
|---|---|---|
| 0764886A2 | 3/1997 | European Pat. Off. . |
| 1-206349 | 8/1989 | Japan . |
| 6-110227 | 4/1994 | Japan . |

*Primary Examiner*—Gary Geist
*Assistant Examiner*—Taylor Victor Oh

*Attorney, Agent, or Firm*—Smith, Gambrell & Russell; Beveridge, DeGrandi, Weilacher & Young Intellecual Property Group

[57] ABSTRACT

The present invention provides a naphthoquinone derivative represented by the general formula (1):

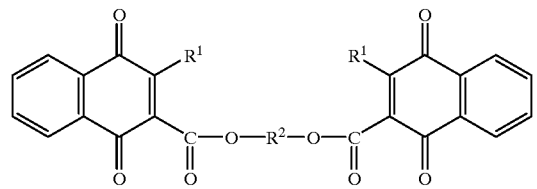

(1)

wherein $R^1$ represents an aryl group which may have a substituent; and $R^2$ represents an alkylene group which may have a substituent, an arylene group which may have a substituent, etc.

5 Claims, 5 Drawing Sheets

NAPHTHOQUINONE DERIVATIVE

BACKGROUND OF THE INVENTION

The present invention relates to a novel naphthoquinone derivative, and an electrophotosensitive material using the same, which is used in image forming apparatuses such as copying machine, facsimile, laser beam printer and the like.

In the above image forming apparatuses, electrophotosensitive materials of various materials are used. The one is an inorganic photoconductor using an inorganic material such as selenium in a photosensitive layer and the other one is an organic photoconductor (OPC) using an organic material in a photosensitive layer. Among them, the organic photoconductor has widely been studied because of a lot of merits such as cheap price, high productivity and no environmental pollution in comparison with the organic photoconductor.

As the organic photoconductor, a multi-layer type (so-called function-separating type) photoconductor comprising an electric charge generating layer and an electric charge-transferring layer, which are laminated, has exclusively been known, but a so-called single-layer type photoconductor wherein an electric charge generating material and an electric charge-transferring material are dispersed in a single photosensitive layer, has also been known.

Those having high carrier mobility are required as the electric charge-transferring material used in these photoconductors. However, almost all of electric charge-transferring materials having high carrier mobility show hole transferring properties. Therefore, the organic photoconductor put into practical use is limited to a negative charging type multi-layer type organic photoconductor provided with an electric charge-transferring layer at the outermost layer in view of the mechanical strength. However, since the negative charging type organic photoconductor utilizes negative-polarity corona discharge, a large amount of ozone is generated and, therefore, problems such as environmental pollution, deterioration of photoconductor, etc. arise.

Therefore, in order to solve these problems, it has been studied to use an electron transferring material as the electric charge-transferring material. In Japanese Patent Laid-Open Publication No. 1-206349, there is suggested that a compound having a diphenoquinone structure or a benzoquinone structure is used as the electron transferring material for electrophotosensitive material.

In Japanese Patent Laid-Open Publication No. 6-110227, there is suggested that a compound having a benzoquinone structure or a naphthoquinone structure is used as the electron transferring material for electrophotosensitive material.

However, since it is difficult to perform matching between a conventional electron transferring materials such as diphenoquinone derivative, benzoquinone derivative, naphthoquinone derivative, etc. and the electric charge generating material, the injection of electrons from the electric charge generating material into the electron transferring material is insufficient. Furthermore, since the electron transferring material has poor compatibility with a resin binder and a hopping distance becomes longer, electron movement at low electric field is dull. Accordingly, a photoconductor containing a conventional electron transferring material had a problem such as high residual potential and low sensitivity, as is apparent from a photosensitivity test described in the following Examples.

As described above, almost all of practical organic photoconductors have a multi-layer type photosensitive layer at present, whereas a photoconductor having a single-layer type photosensitive layer has a simple structure and can be easily produced, and has a lot of merits in view of inhibition of damage in coating of the layer, improvement in the optical characteristics, etc.

And besides, regarding such a photoconductor having a single-layer type photosensitive layer, one photoconductor can be used in both the positive charging and the negative charging types by using the electron transferring material in combination with the hole transferring material, and there is a possibility of increasing applications of the photoconductor. However, since a conventional transferring material has a problem of inhibiting transferring of electrons and holes due to the mutual interaction with the hole transferring material, such a photoconductor having a single-layer type photosensitive layer has not been put to practical use, widely.

SUMMARY OF THE INVENTION

It is an object of the present invention to solve the above technical problems and to provide a novel compound which is suitable as an electron transferring material of an electrophotosensitive material.

It is another object of the present invention to provide an electrophotosensitive material wherein the injection and transferring of electrons from an electric charge generating material are smoothly performed and the sensitivity is improved in comparison with a conventional one.

The present inventors have studied intensively in order to solve the above problems. As a result, it has been found that a naphthoquinone derivative represented by the general formula (1):

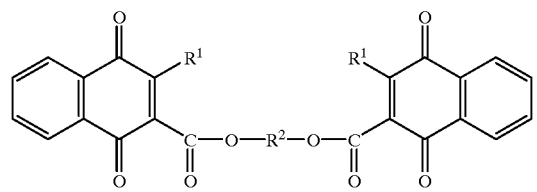

wherein $R^1$ represents an aryl group which may have a substituent; and $R^2$ represents an alkylene group which may have a substituent, an arylene group which may have a substituent, a group (i):

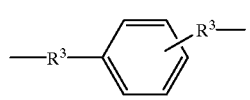

($R^3$ represents an alkylene group which may have a substituent), or a group (ii):

has an electron transferring capability higher than that of a conventional diphenoquinone compound or a nephthoquinone derivative. Thus, the present invention has been accomplished.

The naphthoquinone derivative represented by the above general formula (1) of the present invention is superior in electron acceptance properties because of an action of a group of a naphthoquinone ring: <C=O, and has a good solubility in solvent and compatibility with a resin binder because of an action of the group $R^1$. Accordingly, since the naphthoquinone derivative (1) is superior in matching with the electric charge generating material, the injection of electrons is smoothly performed. Also, since the naphthoquinone derivative is uniformly dispersed in the photosensitive layer, the hopping distance of electrons is short and the electron transferring characteristics in a low electric field exhibit particularly excellent.

Since the naphthoquinone derivative (1) is prepared by combining two naphthoquinone rings, which are intrinsically superior in electron transferring properties and electron acceptance properties, due to an action of the above respective substituents (e.g. carbonyl group, etc.), it is assumed that further improvement in electron transferring characteristics is made.

Accordingly, the electrophotosensitive material of the present invention is characterized by comprising a conductive substrate and a photosensitive layer provided on the conductive substrate, the photosensitive layer containing the naphthoquinone derivative (1) represented by the general formula (1). Consequently, an electrophotosensitive material having high sensitivity can be obtained.

The photosensitive layer containing the naphthoquinone derivative material (1) is particularly superior in electron transferring characteristics in a low electric field and, furthermore, the rate of recombination between electrons and holes in the photosensitive layer is decreased and an apparent electric charge generation efficiency approaches to a actual value. Therefore, the sensitivity of the photosentive material is improved. The residual potential of the photosensitive material is also lowered and, therefore, the stability and durability in case of performing exposure repeatedly are also improved.

Since the naphthoquinone derivative (1) does not cause a mutual interaction with the hole transferring material, which inhibits transferring of electrons and holes, an electrophotosensitive material having higher sensitivity can be constituted when using in the single-layer type photosensitive layer containing a hole transferring material in the same layer.

Furthermore, when the photosensitive layer contains an electron transferring material having a redox potential of from −0.8 to −1.4 V, the sensitivity of the photosensitive material is further improved.

Reason for the improvement is assumed as follows. That is, since the electron transferring material has a function of taking electrons from the electric charge generating material to transmit them to the naphthoquinone derivative (1), the injection of electrons from the electric charge generating material into the naphthoquinone derivative (1) becomes more smooth.

Particularly considering the compatibility, etc. with the naphthoquinone derivative (1), it is preferable to use, as the electron transferring material, a diphenoquinone derivative represented by the general formula (2):

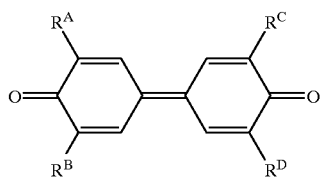

wherein $R^A$, $R^B$, $R^C$ and $R^D$ are the same or different and represent a hydrogen atom, an alkyl group, an alkoxy group, an aryl group, an aralkyl group, a cycloalkyl group or an amino group, or a benzoquinone derivative represented by the general formula (3):

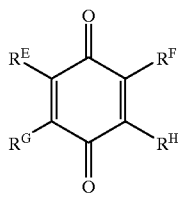

wherein $R^E$, $R^F$, $R^G$ and $R^H$ are the same or different and represent a hydrogen atom, an alkyl group, an alkoxy group, an aryl group, an aralkyl group, a cycloalkyl group, or an amino group which may have a substituent.

The naphthoquinone derivative (1) can also be used in purposes such as solar batteries, EL (electroluminescent) devices, etc. by utilizing its high electron transferring capability.

DETAILED DESCRIPTION OF THE INVENTION

Figure 1:
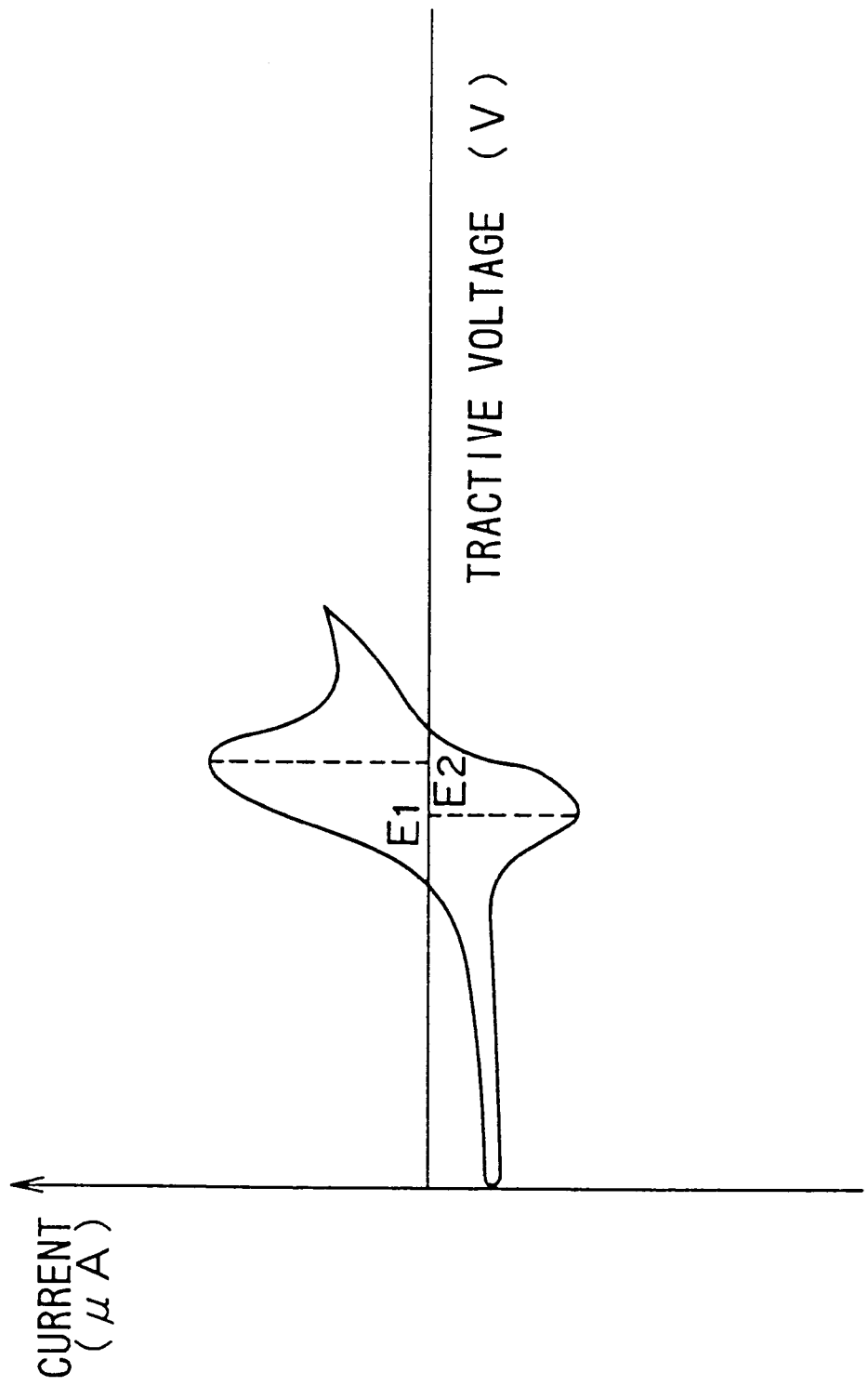
FIG. 1 is a graph illustrating a relationship between the tractive voltage (V) and the current ($\mu$A) for obtaining a redox potential in the present invention.

In the naphthoquinone derivative represented by the general formula (1), examples of the aryl group for the group $R^1$ include phenyl, tolyl, xylyl, biphenyl, o-terphenyl, naphthyl, anthryl, phenanthryl and the like.

Examples of the arylene group for the group $R^2$ include phenylene, naphthylene, anthracenediyl, phenanthrylene and the like.

Examples of the alkylene group for the groups $R^2$ and $R^3$ include groups having 1 to 6 carbon atoms, such as methylene, ethylene, trimethylene, tetramethylene, pentamethylene, hexamethyhlene and the like.

The above alkylene group and arylene group may have a substituent, and examples of the substituent include alkyl group or halogen atom.

The above aryl group may have a substituent, and examples of the substituent include alkyl group, aralkyl group, alkoxy group, alkanoyl group, halogen atom, aryl group, alkoxycarbonyl group and the like.

Examples of the alkyl group include groups having 1 to 6 carbon atoms, such as methyl, ethyl, n-propyl, isopropyl, n-butyl, isobutyl, s-butyl, t-butyl, pentyl, hexyl and the like.

Examples of the halogen atom include fluorine, chlorine, bromine, iodine and the like.

Examples of the alkoxy group include alkoxy groups having 1 to 6 carbon atoms, such as methoxy, ethoxy, propoxy, isopropoxy, butoxy, isobutoxy, s-butoxy, t-butoxy, pentyloxy, hexyloxy and the like.

Examples of the aralkyl group include aralkyl groups of which alkyl portion has 1 to 6 carbon atoms, such as benzyl, 1-phenylethyl, 3-phenylpropyl, 4-phenylbutyl, 5-phenylpentyl, 6-phenylhexyl and the like.

Examples of the alkoxycarbonyl group include alkoxycarbonyl groups of which alkoxy portion has 1 to 6 carbon atoms, such as methoxycarbonyl, ethoxycarbonyl, propoxycarbonyl, isopropoxycarbonyl, butoxycarbonyl, t-butoxycarbonyl, pentyloxycarbonyl, hexyloxycarbonyl and the like.

Examples of the alkanoyl group include alkanoyl groups having 1 to 6 carbon atoms, such as acetyl, propionyl, butylyl, isobutylyl, pentanoyl, t-butylcarbonyl, hexanoyl and the like.

Examples of the aryl group include the same groups as those described above.

Furthermore, the above alkyl and aryl group may have a substituent, and examples of the substituent of the alkyl group include the above halogen atoms. Examples of the substituent of the aryl group include the above alkyl groups or halogen atoms.

A naphthoquinone derivative wherein the group $R^2$ is an alkylene group is particularly superior in electron transferring capability, and a photoconductor having higher sensitivity can be obtained.

A naphthoquinone derivative wherein the group $R^2$ is the above group (i), group (ii) or arylene group can improve transition temperature Tg of the photosensitive layer because of high glass transition temperature Tg. For example, there is an effect of preventing a pressure-welded trace from being formed on the surface of the photosensitive material at the time of stopping of the apparatus by a cleaning blade pressure-welded on the surface of the photosensitive material. Those wherein the above arylene group is substituted with an alkyl group as the substituent are particularly superior in solubility in solvent and compatibility with a binder resin.

Specific examples of the naphthoquinone derivative (1) represented by the general formula (1) include compounds represented by the following formulas (1-1) to (1–6).

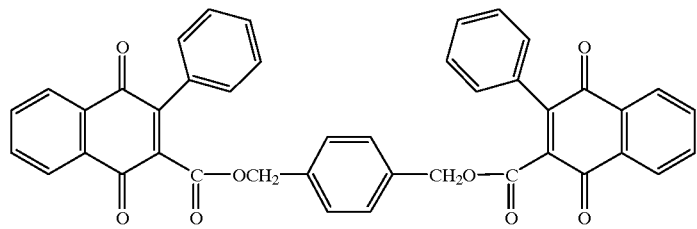

(1-1)

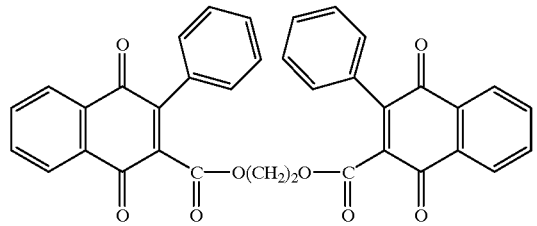

(1-2)

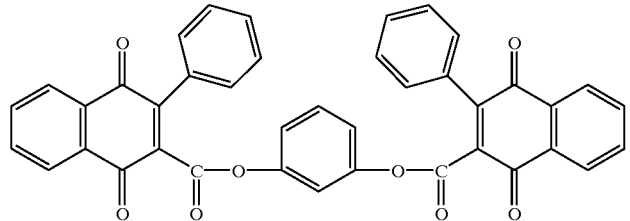

(1-3)

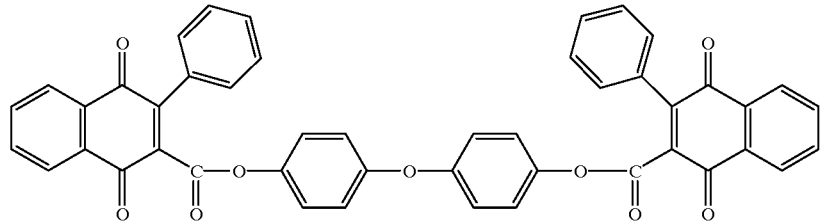

(1-4)

-continued

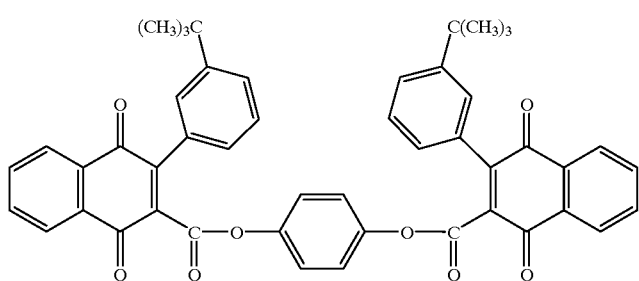

(1-5)

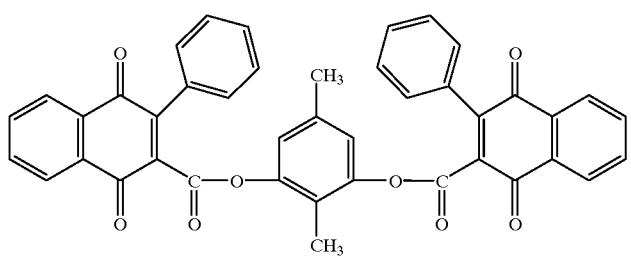

(1-6)

The naphthoquinone derivative represented by the general formula (1) is synthesized as shown in the following reaction schemes I to III.

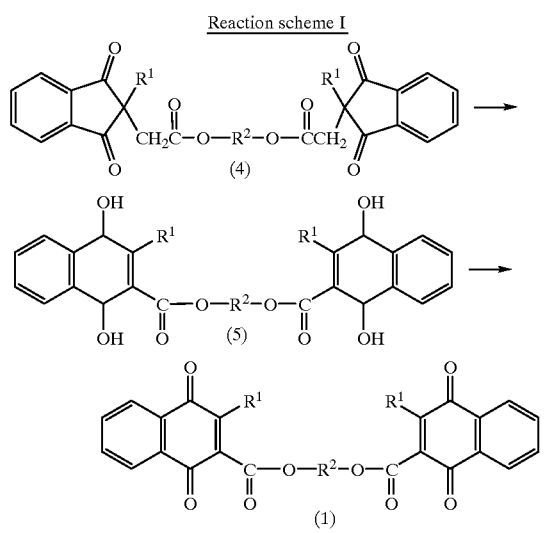

Reaction scheme I wherein $R^1$ and $R^2$ are as defined above.

According to this reaction scheme, the naphthoquinone derivative (1) of the present invention is obtained by isomerizing an acetate of a 1,3-indandione derivative represented by the general formula (4) in a suitable solvent or no solvent in the presence of sodium hydride to obtain a 1,4-dihydroxynaphthalene derivative represented by the general formula (5) and oxidizing the 1,4-dihydroxynaphthalene derivative.

An amount of the sodium hydride used is at least 2 mol, preferably 2.5 mol, per mol of the above compound (4).

The reaction is usually performed at 40 to 100° C., preferably 70 to 80° C., and is completed in about 4 hours.

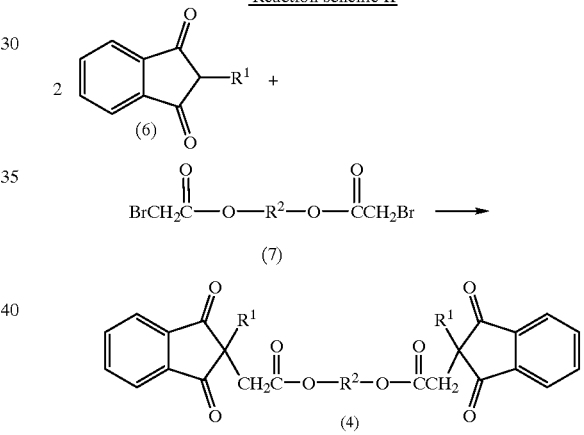

Reaction scheme II wherein $R^1$ and $R^2$ are as defined above.

According to this reaction, the compound of the above formula (4) as the raw material of the above reaction scheme I is obtained by reacting a 1,3-indandione derivative represented by the general formula (6) with dibromoacetate represented by the general formula (7) in a suitable solvent or no solvent in the presence of a base.

Examples of the base include sodium alkoxides such as sodium methoxide, etc.; and metal hydrides such as sodium hydride, etc.

An amount of the base used is at least an equimolar amount, preferably 1.2 mol, per mol of the derivative of the general formula (6).

The reaction is performed usually at 40 to 100° C., preferably 70 to 80° C., and is completed in about 5 hours.

Reaction scheme III

HO—R²—OH + 2 CH₂BrCOOH ⟶
(8)             (9)

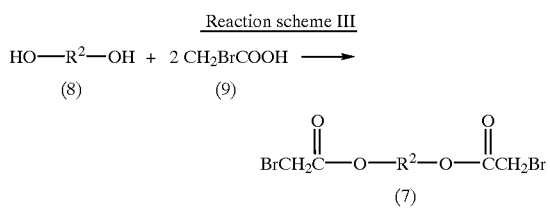
(7)

wherein R² is as defined above.

According to this reaction, the compound of the above formula (7) as the starting material of the above reaction scheme II is obtained by reacting diols represented by the general formula (8) with bromoacetic acid represented by the general formula (9) in a proper solvent or without solvent in the presence of an acid catalyst.

As the acid catalyst, a general catalyst for esterification is used, and specific examples thereof include inorganic acids such as hydrochloric acid, concentrated sulfuric acid, phosphoric acid, polyphosphoric acid, boron trifluoride, perchloric acid, etc.; organic acids such as p-toluenesulfonic acid, benzenesulfonic acid, trichloromethanesulfonic acid, etc.; and trifluoromethanesulfonic anhyride.

It is also possible to use a condensing agent such as 1,1'-carbonylbis-1H-imidazole, dicyclohexylcarbodiimide, etc. in place of the above acid catalyst.

The reaction is performed usually at 40 to 150° C., preferably 40 to 120° C., and is completed in about 4 hours.

Examples of the above solvent include benzene, methylene chloride, chloroform, tetrahydrofuran, dimethylformamide, dimethyl sulfoxide and the like.

The electrophotosensitive material of the present invention will be described hereinafter.

The electrophotosensitive material of the present invention is that obtained by providing a photosensitive layer on a conductive substrate, said photosensitive layer containing, as an electron transferring material, the naphthoquinone derivative (1) represented by the above general formula (1) in a resin binder.

The above electrophotosensitive material may be a single-layer type or a multi-layer type, but the effect of use of the electron transferring material appears remarkably in the single-layer type.

The single-layer type electrophotosensitive material is that obtained by providing a single photosensitive layer on a conductive substrate, said photosensitive layer comprising a resin binder containing a naphthoquinone derivative (1) as an electron transferring material, together with at least an electric charge generating material and a hole transferring material.

This single-layer type photosensitive material can be applied to both positive charging and negative charging type, but is preferably used as the positive charging type.

On the other hand, the multi-layer type electrophotosensitive material is that obtained by providing at least an electric charge generating layer and an electric charge-transferring material on a conductive substrate in this sequence, said electric charge-transferring layer containing a naphthoquinone derivative (1) as an electron transferring material. Regarding this multi-layer type electrophotosensitive material, a residual potential is largely lowered in comparison with a conventional multi-layer type electrophotosensitive material and the sensitivity is improved. In order to smoothly perform the giving and receiving of electrons from the electric charge generating layer to the electric charge-transferring layer, the naphthoquinone derivative (1) is also contained in the electric charge generating layer, preferably.

Since the naphthoquinone derivative used in the electrophotosensitive material of the present invention is not only superior in solubility in solvent and compatibility with a resin binder, but also superior in matching with the electric charge generating material, as described above, the injection of electrons is smoothly performed and the electron transferring characteristics in a low electric field are particularly excellent.

Accordingly, in the positive charging type single-layer type photosensitive material, electrons emitted from the electric charge generating material in the process of exposure are smoothly injected into the electron transferring material of the naphthoquinone derivative represented by the above general formula (1). Then, electrons are transported to the surface of the photosensitive layer by means of the giving and receiving of electrons between electron transferring materials to cancel the positive electric charge (+) which has previously been charged on the surface of the photosensitive layer. On the other hand, holes (+) are injected into the hole transferring material and transported to the surface of the conductive substrate without being trapped on the way, thereby canceling the negative charge (−) on the surface of the conductive substrate. It is considered that the sensitivity of the positive charging type single-layer type photosensitive material is improved in such a manner. In the negative single-layer type photosensitive layer, the direction of the transferring of charges is only reversed to the above direction and the sensitivity is also improved.

In the positive charging type multi-layer type photosensitive material, electrons emitted from the electric charge generating material of the electric charge generating layer in the exposure step are smoothly injected into the electron transferring material of the naphthoquinone derivative represented by the above general formula (1). Then, electrons are transferred in the electric charge-transferring layer and reached the surface of the photosensitive layer by means of the giving and receiving of electrons between electron transferring materials to cancel the positive electric charge (+) which has previously been charged on the surface of the photosensitive layer. On the other hand, holes (+) are transferred directly to the surface of the conductive substrate from the electric charge generating layer to cancel the negative charge (−) on the surface of the conductive substrate. It is considered that the sensitivity of the positive charging type multi-layer type photosensitive material is improved in such a manner.

The electric charge generating material which absorbs light by exposure to the photosensitive material forms a pair of ions [hole (+) and electron (−)]. The probability that a pair of ions are recombined to disappear may be small so that a pair of ions formed is converted into a free carrier to effectively cancel the surface charge.

In the electrophotosensitive material of the present invention, the other electron transferring material can be used in combination with the above naphthoquinone derivative (1). An electron transferring material having a redox potential of from −0.8 to −1.4 V is used, particularly preferably. The reason is considered as follows.

When using the electron transferring material having a redox potential of −1.4 V or less, the energy level of LUMO (which means the orbital of which energy level is most low in molecular orbitals containing no electrons, and the excited electrons normally transfer to this orbital) becomes higher than that of the electric charge generating material. Therefore, electrons are not transferred to the electron transferring material in case of forming a pair of ions, which does not lead to an improvement in efficiency of the electric charge generation.

To the contrary, when using the electron transferring material having a redox potential of −1.4 V or more, the energy level of LUMO is lower than that of the electric charge generating material. Therefore, electrons are transferred to the electron transferring material in case of forming a pair of ions and a pair of ions is easily separated to the carrier. That is, the electron transferring material acts on charge generation to improve the efficiency of the electron charge generation.

Furthermore, it is also necessary to cause no carrier trapping due to impurities at the time of transferring of the free carrier so that the photosensitive material may have high sensitivity.

Normally, trapping due to a small amount of impurities exists in the transfer process of free carriers, and free carriers transfer while causing trapping-detrapping repeatedly. Accordingly, when using the electron transferring material having a redox −0.8 or more, free carriers are fallen into the level where detrapping can not be effected and carrier trapping arises so that the transferring is stopped.

To the contrary, when using the electron transferring material having a redox potential of −0.8 or less, no carrier trapping arises and the transferring of free carriers is easily performed.

As shown in FIG. 1, $E_1$ and $E_2$ shown in the same figure were determined from a relationship between an tractive (V) and a current (μA), and then the redox potential was calculated by using the following equation:

Redox potential (V)=$(E_1+E_2)/2$

The above tractive (V) and current (μA) were measured by means of a three-electrode system cyclic voltametry using the following materials.

Electrode: work electrode (glassy carbon electrode), counter electrode (platinum electrode)
Reference electrode: silver nitrate electrode
(0.1 mol/l AgNO$_3$-CH$_3$CN solution)
Measuring solution:
Electrolyte: tetra-n-butylammonium perchlorate (0.1 mols)
Measuring substance: electron transferring material(0.001 mols)
Solvent: CH$_2$Cl$_2$ (1 litter)
The measuring solution is prepared by mixing the above materials.

Such an electron transferring material may be any compound whose redox potential is within the range from −0.8 to −1.4 V, and is not specifically limited. Examples thereof include compounds such as benzoquinone compound, naphthoquinone compound, anthraquinone compound, diphenoquinone compound, malononitrile compound, thiopyran compound, 2,4,8-trinitrothioxanthone, fluorenone compound such as 3,4,5,7-tetranitro-9-fluorenone, etc., dinitroanthracene, dinitroacridine, nitroanthraquinone and dinitroanthraquinone.

Considering the compatibility with the electric charge generating material or naphthoquinone derivative (1) of the present invention, among the above respective compounds, compounds which belong to the diphenoquinone compound represented by the above general formula (2) or benzoquinone compound represented by the general formula (3) and have a redox potential within the above range are used, most preferably.

Among $R^A$, $R^B$, $R^C$ and $R^D$ in the above formula, two or more groups of them are preferably the same groups, but are not limited thereto.

Example of the alkyl group, aralkyl group, alkoxy group and aryl group in the above formula include the same groups as those described above.

Examples of the cycloalkyl group include cycloalkyl groups having 3 to 6 carbon atoms, such as cyclopropyl, cyclobutyl, cyclopentyl, cyclohexyl and the like.

Examples of the amino group which may have a substituent include monomethylamino, dimethylamino, monoethylamino, diethylamino, etc., in addition to amino.

Specific examples of the diphenoquinone compound include 3,5-dimethyl-3',5'-di(t-butyl)-4,4'-diphenoquinone (redox potential: −0.86 V) represented by the formula (2-1), 3,5,3',5'-tetrakis(t-butyl)-4,4'-diphenoquinone (redox potential: −0.94 V) represented by the formula (2-2), etc., but are not limited thereto.

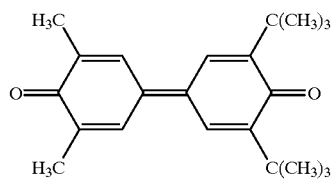

(2-1)

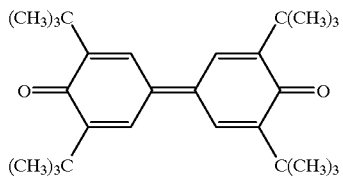

(2-2)

Specific examples of the benzoquinone compound include p-benzoquinone (redox potential: −0.81 V) represented by the formula (3-1), 2,6-di(t-butyl)-p-benzoquinone (redox potential: −1.31 V) represented by the formula (3-2), etc., but are not limited thereto.

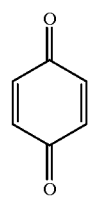

(3-1)

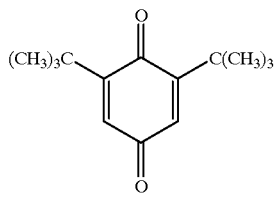

(3-2)

These electron transferring materials can be used alone or in combination thereof.

In the present invention, other electron transferring materials, which have hitherto been known, may be contained in the photosensitive layer, in addition to the above electron transferring material. Examples thereof include compounds represented by the following general formulas (ET1) to (ET16):

(ET1)

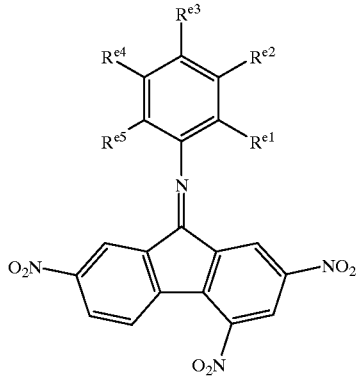

wherein $R^{e1}$, $R^{e2}$, $R^{e3}$, $R^{e4}$ and $R^{e5}$ are the same or different and represent a hydrogen atom, an alkyl group which may have a substituent, an alkoxy group which may have a substituent, an aryl group which may have a substituent, an aralkyl group which may have a substitient, a phenoxy group which may have a substituent, or a halogen atom, (ET2)

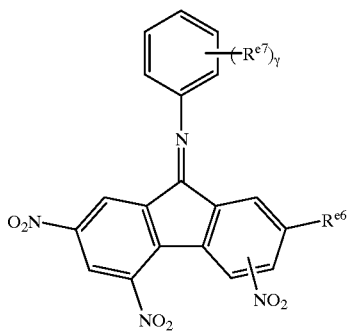

wherein $R^{e6}$ represents an alkyl group; $R^{e7}$ represents an alkyl group which may have a substituent, an alkoxy group which may have a substituent, an aryl group which may have a substituent, an aralkyl group which may have a substitient, a halogen atom or a halogenated alkyl group; and γ represents an integer of 0 to 5; provided that each of $R^{e7}$ may be different when γ is 2 or more, (ET3)

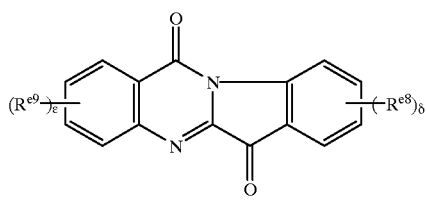

wherein $R^{e8}$ and $R^{e9}$ may be the same or different and represent an alkyl group: δ represents an integer of 1 to 4; and ε represents an integer of 0 to 4; provided that each of $R^{e8}$ and $R^{e9}$ may be different when δ and ε are 2 or more, (ET4)

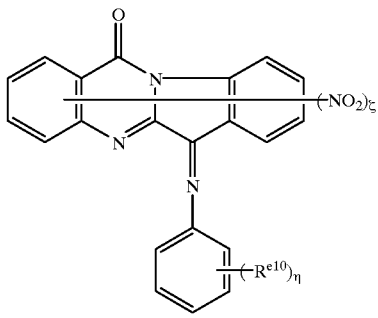

wherein $R^{e10}$ represents an alkyl group, an aryl group, an aralkyl group, an alkoxy group, a halogenated alkyl group or a halogen atom; ζ represents an integer of 0 to 4; and η represents an integer of 0 to 5; provided that each of $R^{e10}$ may be different from one another when η is 2 or more, (ET5)

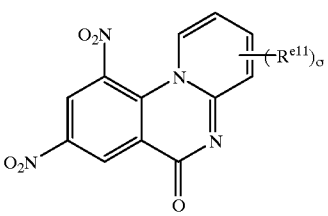

wherein $R^{e11}$ represents an alkyl group; and σ represents an integer of 1 to 4; provided that each of $R^{e11}$ may be different from one another when σ is 2 or more, (ET6)

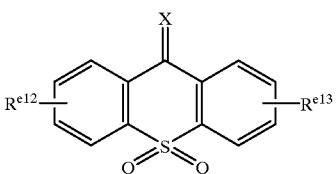

wherein $R^{e12}$ and $R^{e13}$ are the same or different and represent a hydrogen atom, a halogen atom, an alkyl group, an aryl group, an aralkyloxycarbonyl group, an alkoxy group, a hydroxyl group, a nitro group or a cyano group; and X represents an oxygen atom, a =N—CN group or a =C(CN)$_2$ group, (ET7)

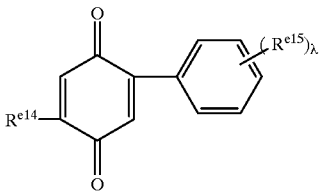

wherein $R^{e14}$ represents a hydrogen atom, a halogen atom, an alkyl group or a phenyl group which may have a substituent; $R^{e15}$ represents a halogen atom, an alkyl group which may have a substituent, a phenyl group which may have a substituent, an alkoxycarbonyl group, an N-alkylcarbamoyl group, a cyano group or a nitro group; and λ represents an integer of 0 to 3; provided that each of $R^{e15}$ may be different from one another when λ is 2 or more,

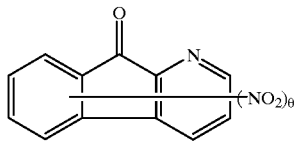 (ET8)

wherein θ represents an integer of 1 to 2,

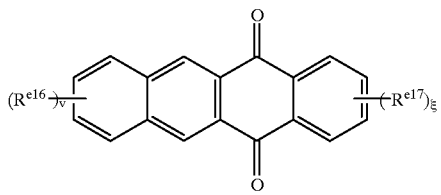 (ET9)

wherein $R^{e16}$ and $R^{e17}$ are the same or different and represent a halogen atom, an alkyl group which may have a substituent, a cyano group, a nitro group or an alkoxycarbonyl group; and ν and ξ respectively represent an integer of 0 to 3; provided each of $R^{e16}$ may be different when either of ν or ξ is 2 or more, and the same is true for $Re^{e17}$,

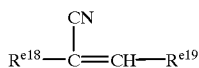 (ET10)

wherein $R^{e18}$ and $R^{e19}$ are the same or different and represent a phenyl group, a polycyclic aromatic group or a heterocyclic group, and these groups may respectively have a substituent,

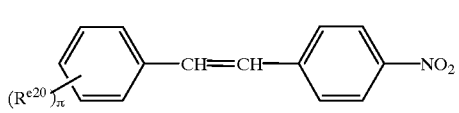 (ET11)

wherein $R^{e20}$ represents an amino group, a dialkylamino group, an alkoxy group, an alkyl group or a phenyl group; and π represents an integer of 1 to 2; provided that each of $R^{e20}$ may be different from one another when π is 2,

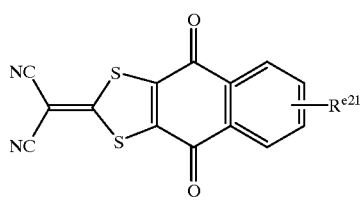 (ET12)

wherein $R^{e21}$ represents a hydrogen atom, an alkyl group, an aryl group, an alkoxy group or an aralkyl group,

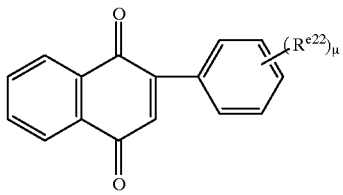 (ET13)

wherein $R^{e22}$ represents a halogen atom, an alkyl group which may have a substituent, a phenyl group which may have a substituent, an alkoxycarbonyl group, a N-alkylcarbamoyl group, a cyano group or a nitro group; and μ represents an integer of 0 to 3; provided that each of $R^{e22}$ may be different from one another when μ is 2 or more,

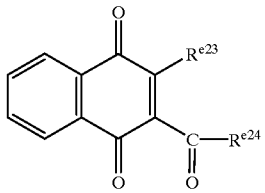 (ET14)

wherein $R^{e23}$ represents an alkyl group which may have a substituent, or an aryl group which may have a substituent; and $R^{e24}$ represents an alkyl group which may have a substituent, an aryl which may have a substituent, or a group: —O—$R^{e24a}$ ($R^{e24a}$ represents an alkyl group which may have a substituent, or an aryl group which may have a substituent),

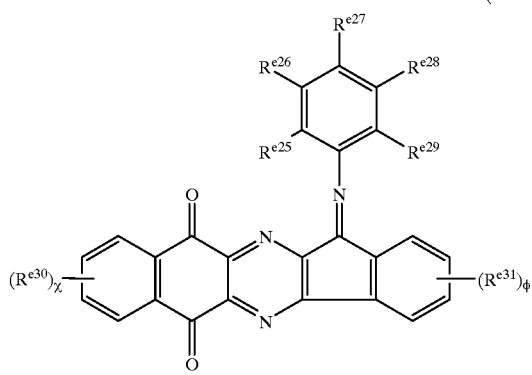 (ET15)

wherein $R^{e25}$, $R^{e26}$, $R^{e27}$, $R^{e28}$, $R^{e29}$, $R^{e30}$ and $R^{e31}$ are the same or different and represent an alkyl group, aryl group, aralkyl group, alkoxy group, a halogen atom or a halogenated alkyl group; and χ and φ are the same or different and represent an integer of 0 to 4,

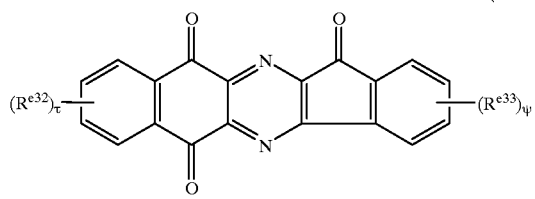

(ET16)

wherein $R^{e32}$ and $R^{e33}$ are the same or different and represent an alkyl group, an aryl group, an alkoxy group, a halogen atom or a halogenated alkyl group; and τ and φ are the same or different and represent an integer of 0 to 4.

In the above electron transferring materials, examples of the alkyl group, aryl group, alkoxycarbonyl group, aralkyl group, alkoxy group, halogen atom and cycloalkyl group include the same groups as those described above.

Examples of the heterocyclic group include thienyl, furyl, pyrrolyl, pyrrolidinyl, oxazolyl, isoxazolyl, thiazolyl, isothiazolyl, imidazolyl, 2H-imidazolyl, pyrazolyl, triazolyl, tetrazolyl, pyranyl, pyridyl, piperidyl, piperidino, 3-morpholinyl, morpholino, thiazolyl and the like. In addition, it may be a heterocyclic group condensed with an aromatic ring.

Examples of the halogenated alkyl group include halogenated alkyl groups of which alkyl portion has 1 to 6 carbon atoms, such as chloromethyl, bromomethyl, fluoromethyl, iodomethyl, 2-chloroethyl, 1-fluoroethyl, 3-chloropropyl, 2-bromopropyl, 1-chloropropyl, 2-chloro-1-methylethyl, 1-bromo-1-methylethyl, 4-iodobutyl, 3-fluorobutyl, 3-chloro-2-methylpropyl, 2-iodo-2-methylpropyl, 1-fluoro-2-methylpropyl, 2-chloro-1,1-dimethylethyl, 2-bromo-1,1-dimethylethyl, 5-bromopentyl, 4-chlorohexyl and the like.

Examples of the polycyclic aromatic group include nephthyl, penanthryl and anthryl and the like.

Examples of the aralkyloxycarbonyl group include those of which aralkyl portions are various aralkyl groups described above.

Examples of the N-alkylcarbamoyl group include those of which alkyl portions are various alkyl groups described above.

Examples of the dialkylamino group include those of which alkyl portions are various alkyl groups described above. Two alkyl groups substituted on the amino may be the same or different.

Examples of the substituent, which may be substituted on each group described above, include halogen atom, amino group, hydroxyl group, optionally esterified carboxyl group, cyano group, alkyl group having 1 to 6 carbon atoms, alkoxy group having 1 to 6 carbon atoms, alkenyl having 2 to 6 carbon atoms which may have an aryl group and the like. The substitution position of the substituent is not specifically limited.

In the present invention, there can be used electron transferring materials, which have hitherto been known, such as benzoquinone compound, malononitrile, thiopyran compound, tetracyanoethylene, 2,4,8-trinitrothioxanthone, dinitrobenzene, dinitroanthracene, dinitroacridine, nitroanthraquinone, dinitroanthraquinone succinic anhydride, maleic anhydride, dibromomaleic anhydride, etc., in addition to those described above.

The electric charge generating material, hole transferring material and resin binder used in the electrophotosensitive material of the present invention are as follows.

<Electric Charge Generating Material>

Examples of the electric charge generating material include compounds represented by the following general formulas (CG1) to (CG12).

(CGI) Metal-free phthalocyanine

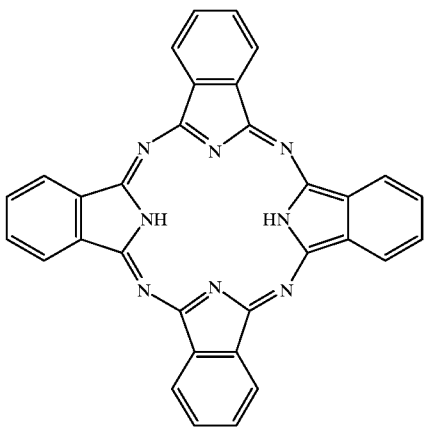

(CG1)

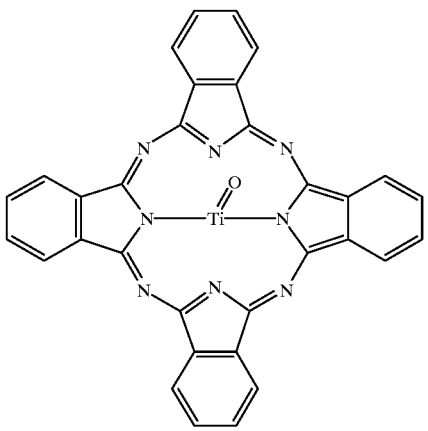

(CG2) Oxotitanyl phthalocyanine

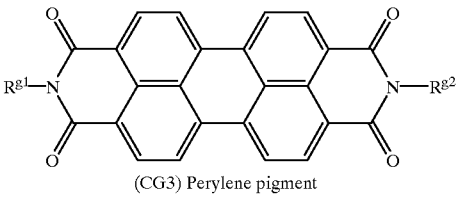

(CG3) Perylene pigment wherein $R^{g1}$ and $R^{g2}$ are the same or different and represent a substituted or an unsubstituted alkyl group having 18 or less carbon atoms, a cycloalkyl group, an aryl group, an alkanoyl group or an aralkyl group.

(CG4) Bisazo pigment $$CP^1\text{—}N\text{=}N\text{—}Q\text{—}N\text{=}N\text{—}CP^2 \quad (CG4)$$

wherein $Cp^1$ and $Cp^2$ are the same or different and represent a coupler residue; and Q represents a group represented by the following formula:

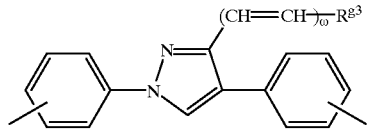
(Q-1)

($R^{g3}$ represents a hydrogen atom, an alkyl group, an aryl group or a heterocyclic group, and the alkyl group, aryl group or heterocyclic group may have a substituent; and ω represents 0 or 1),

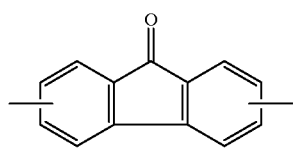
(Q-2)

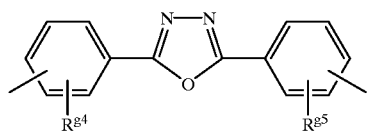
(Q-3)

($R^{g4}$ and $R^{g5}$ are the same or different and represent a hydrogen atom, an alkyl group having 1 to 5 carbon atoms, a halogen atom, an alkoxy group, an aryl group or an aralkyl group),

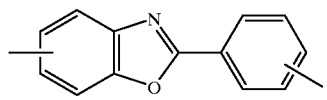
(Q-4)

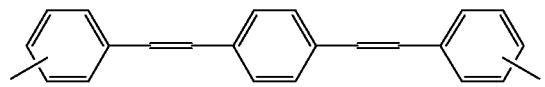
(Q-5)

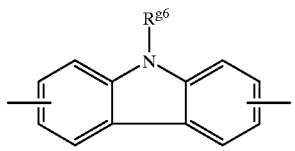
(Q-6)

($R^{g6}$ represents a hydrogen atom, an ethyl group, a chloroethyl group or a hydroxyethyl group), or

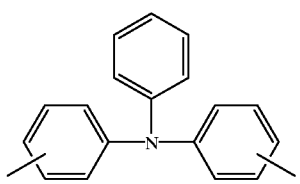
(Q-7)

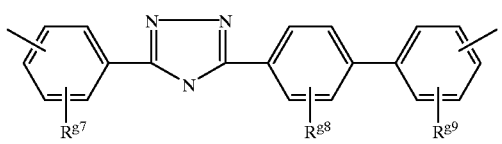
(Q-8)

($R^{g7}$, $R^{g8}$ and $R^{g9}$ are the same or different and represent a hydrogen atom, an alkyl group having 1 to 5 carbon atoms, a halogen atom, an alkoxy group, an aryl group or an aralkyl group)

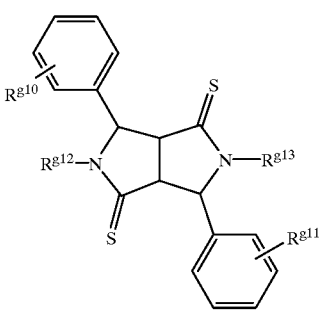
(CG5)

(CG5) Dithioketopyrrolopyrrole pigment wherein $R^{g10}$ and $R^{g11}$ are the same or different and represent a hydrogen atom, an alkyl group, an alkoxy group or a halogen atom; and $R^{g12}$ and $R^{g13}$ are the same or different and represent a hydrogen atom, an alkyl group or an aryl group.

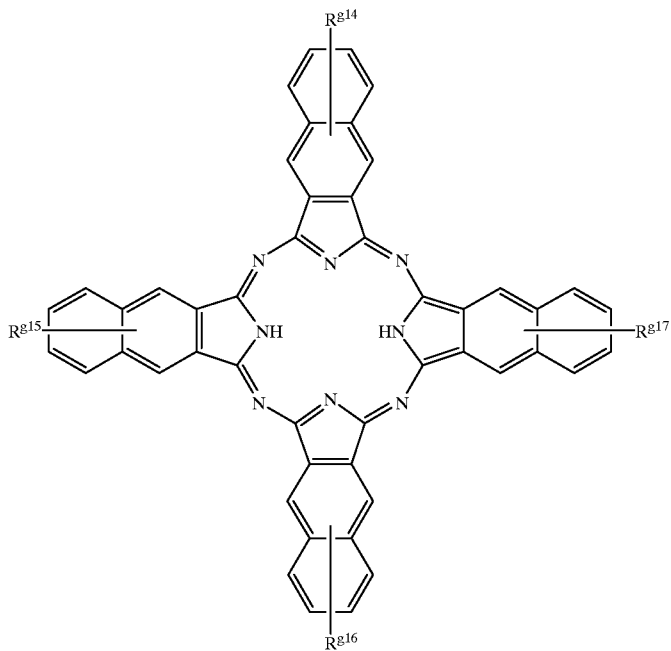

(CG6) Metal-Free naphthalocyanine pigment wherein $R^{g14}$, $R^{g15}$, $R^{g16}$ and $R^{g17}$ are the same or different and represent a hydrogen atom, an alkyl group, an alkoxy group or a halogen atom.

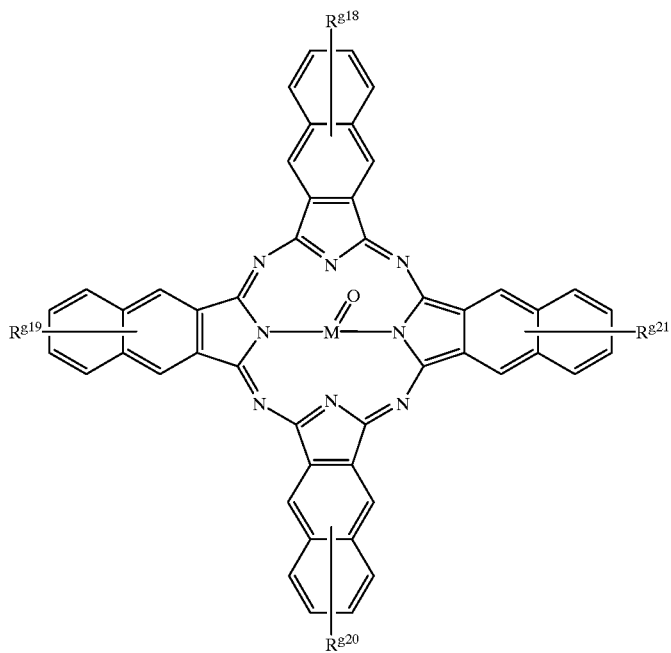

(CG7) Metal phthalocyanine pigment wherein $R^{g18}$, $R^{g19}$, $R^{g20}$ and $R^{g21}$ are the same or different and represent a hydrogen atom, an alkyl group, an alkoxy group or a halogen atom; and M represents Ti or V.

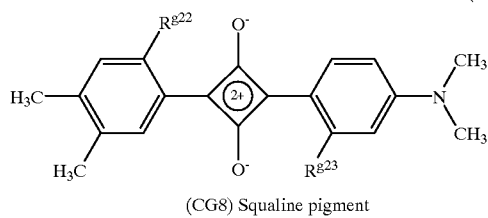

(CG8) Squaline pigment wherein $R^{g22}$ and $R^{g23}$ are the same or different and represent a hydrogen atom, an alkyl group, an alkoxy group or a halogen atom.

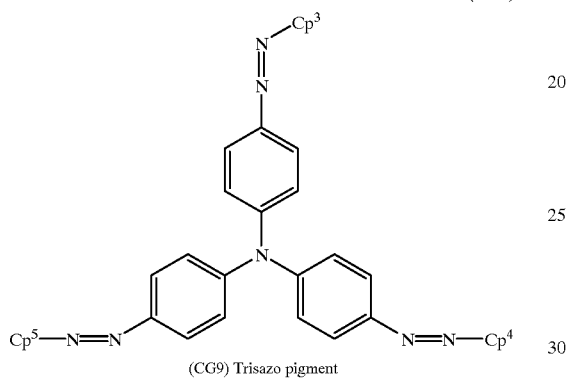

(CG9) Trisazo pigment wherein $Cp^3$, $Cp^4$ and $Cp^5$ are the same or different and represent a coupler residue.

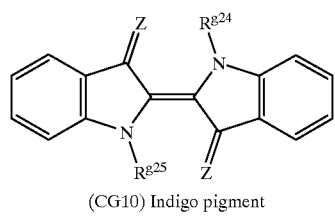

(CG10) Indigo pigment wherein $R^{g24}$ and $R^{g25}$ are the same or different and represent a hydrogen atom, an alkyl group or an aryl group; and Z is an oxygen atom or a sulfur atom.

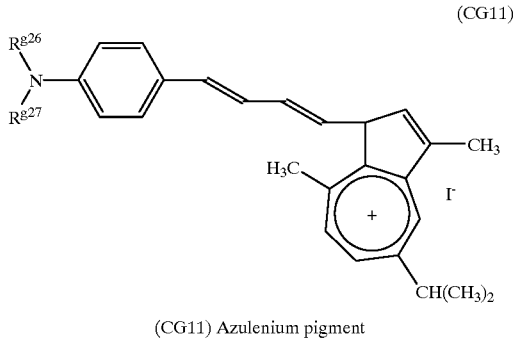

(CG11) Azulenium pigment wherein $R^{g26}$ and $R^{g27}$ are the same or different and represent a hydrogen atom, an alkyl group or an aryl group.

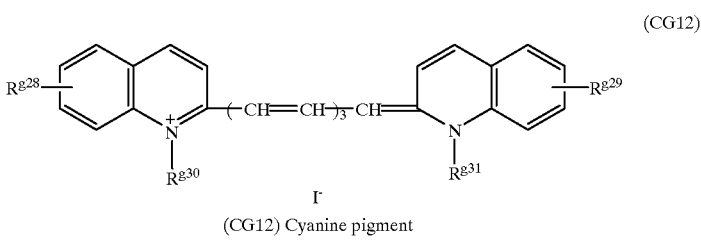

(CG12) Cyanine pigment wherein $R^{g28}$ and $R^{g29}$ are the same or different and represent a hydrogen atom, an alkyl group, an alkoxy group or a halogen atom; and $R^{g30}$ and $R^{g31}$ are the same or different and represent a hydrogen atom, an alkyl group or an aryl group.

In the above electric charge generating material, examples of the alkyl group include substituted or non-substituted alkyl groups having 18 or less carbon atoms, such as octyl, nonyl, decyl, dodecyl, tridecyl, pentadecyl, octadecyl, etc., in addition to the above alkyl groups having 1 to 6 carbon atoms.

Examples of the cycloalkyl group, alkoxy group, alkanoyl group, heterocyclic group, aryl group and aralkyl group include the same groups as those described above.

Examples of the substituent which may be substituted on the above groups include halogen atom, amino group, hydroxyl group, optionally esterified carboxyl group, cyano Examples of the coupler residue represented by $Cp^1$, $Cp^2$, $Cp^3$, $Cp^4$ and $Cp^5$ include the groups shown in the following formulas (Cp-1) to (Cp-11).

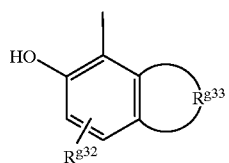
(Cp-1)

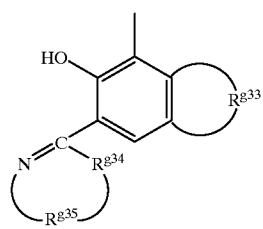
(Cp-2)

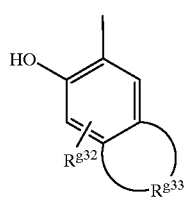
(Cp-3)

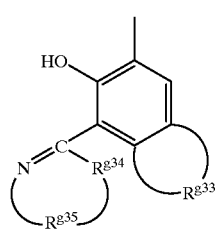
(Cp-4)

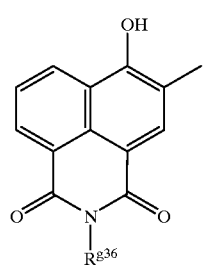
(Cp-5)

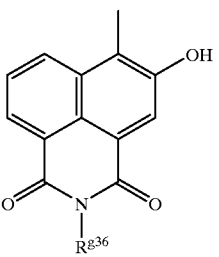
(Cp-6)

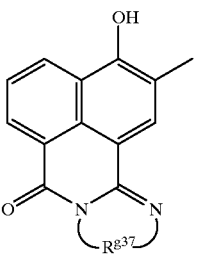
(Cp-7)

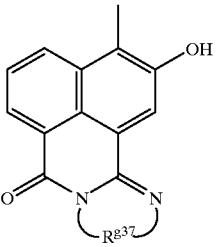
(Cp-8)

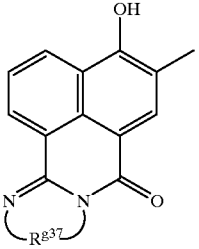
(Cp-9)

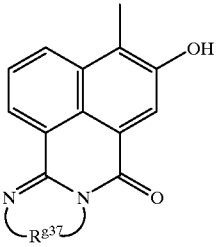
(Cp-10)

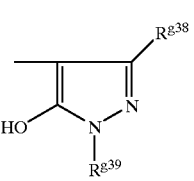
(Cp-11)

In the respective formulas, $R^{g32}$ is a carbamoyl group, a sulfamoyl group, an allophanoyl group, oxamoyl group, anthraninoyl group, carbazoyl group, glycyl group, hydantoyl group, phthalamoyl group or a succinamoyl group. These groups may have substituents such as halogen atom, phenyl group which may have a substituent, naphthyl group which may have a substituent, nitro group, cyano group, alkyl group, alkenyl group, carbonyl group, carboxyl group and the like.

$R^{g33}$ is an atomic group which is required to form an aromatic ring, a polycyclic hydrocarbon or a heterocycle by condensing with a benzene ring, and these rings may have the same substituents as that described above.

$R^{g34}$ is an oxygen atom, a sulfur atom or an imino group.

$R^{g35}$ is a divalent chain hydrocarbon or aromatic hydrocarbon group, and these groups may have the same substituents as that described above.

$R^{g36}$ is an alkyl group, an aralkyl group, an aryl group or a heterocyclic group, and these groups may have the same substituents as that described above.

$R^{g37}$ is an atomic group which is required to form a heterocycle, together with a divalent chain hydrocarbon group or adivalent aromatic hydrocarbon group or two nitrogen atoms in the above formulas (Cp-1) to (Cp-2), and these rings may have the same substituents as that described above.

$R^{g38}$ is a hydrogen atom, an alkyl group, an amino group, a carbamoyl group, a sulfamoyl group, an allophanoyl group, a carboxyl group, an alkoxycarbonyl group, an aryl group or a cyano group, and the groups other than a hydrogen atom may have the same substituents as that described above.

$R^{g39}$ is an alkyl group or an aryl group, and these groups may have the same substituents as that described above.

Examples of the alkenyl group include alkenyl groups having 2 to 6 carbon atoms, such as vinyl, allyl, 2-butenyl, 3-butenyl, 1-methylallyl, 2-pentenyl, 2-hexenyl and the like.

In the above $R^{g33}$, examples of the atomic group which is required to form an aromatic ring by condensing with a benzene ring include alkylene groups having 1 to 4 carbon atoms, such as methylene, ethylene, trimethylene, tetramethylene and the like.

Examples of the aromatic ring to be formed by condensing the above $R^{g33}$ with a benzene ring include naphthalene ring, anthracene ring, phenanthrene ring, pyrene ring, chrysene ring, naphthacene ring and the like.

In the above $R^{g33}$, examples of the atomic group which is required to form a polycyclic hydrocarbon by condensing with a benzene ring include the above alkylene groups having 1 to 4 carbon atoms, or carbazole ring, benzocarbazole ring, dibenzofuran ring and the like.

In the above $R^{g33}$, examples of the atomic group which is required to form a heterocycle by condensing with a benzene ring include benzofuranyl, benzothiophenyl, indolyl, 1H-indolyl, benzoxazoyl, benzothiazolyl, 1H-indadolyl, benzoimidazolyl, chromenyl, chromanyl, isochromanyl, quinolinyl, isoquinolinyl, cinnolinyl, phthalazinyl, quinazolinyl, quinoxalinyl, dibenzofranyl, carbazolyl, xanthenyl, acridinyl, phenanthridinyl, phenazinyl, phenoxazinyl, thianthrenyl and the like.

Examples of the aromatic heterocyclic group to be formed by condensing the above $R^{g33}$ and the benzene ring include thienyl, furyl, pyrrolyl, oxazolyl, isoxazolyl, thiazolyl, isothiazolyl, imidazolyl, pyrazolyl, triazolyl, tetrazolyl, pyridyl, thiazolyl and the like. In addition, it may also be a heterocyclic group condensed with other aromatic rings (e.g. benzofuranyl, benzoimidazolyl, benzoxazolyl, benzothiazolyl, quinolyl, etc.).

In the above $Rg^{35}$ and $R^{g37}$, examples of the divalent chain hydrocarbon include ethylene, trimethylene, tetramethylene and the like. Examples of the divalent aromatic hydrocarbon include phenylene, naphthylene, phenanthrilene and the like.

In the above $R^{g36}$, examples of the heterocyclic group include pyridyl, pyrazyl, thienyl, pyranyl, indolyl and the like.

In the above $R^{g37}$, examples of the atomic group which is required to form a heterocycle, together with two nitrogen atoms, include phenylene, naphthylene, ethylene, trimethylene, tetramethylene and the like.

Examples of the aromatic heterocyclic group to be formed by the above $R^{g37}$ and two nitrogen atoms include benzoimidazole, benzo[f]benzoimidazole, dibenzo[e,g] benzoimidazole, benzopyrimidine and the like. These groups may respectively have the same group as that described above.

In the above $R^{g38}$, examples of the alkoxycarbonyl group include methoxycarbonyl, ethoxycarbonyl, propoxycarbonyl, butoxycarbonyl and the like.

In the present invention, there can be used powders of inorganic photoconductive materials such as selenium, selenium-tellurium, cadmium-sulfide, amorphous silicon, etc. and electric charge generating materials, which have hitherto been known, such as pyrilium salt, anthanthrone pigments, triphenylmethane pigments, threne pigments, toluidine pigments, pyrazoline pigments, quinacridone pigments, etc., in addition to the above electric charge generating materials.

The above electric charge generating materials can be used alone or in combination thereof to present an absorption wavelength within a desired range.

Among the above electric charge generating materials, a photosensitive material having sensitivity at the wavelength range of 700 nm or more is required in digital-optical image forming apparatuses such as laser beam printer using a light source of semiconductor laser, facsimile, etc. Therefore, phthalocyanine pigments such as metal-free phthalocyanine represented by the above generoxoformula (CG1), oxotitanyl phthalocyanine represented by the general formula (CG2), etc. are preferably used. The crystal form of the above phthalocyanine pigments is not specifically limited, and various phthalocyanine pigments having different crystal form can be used.

In analogue-optical image forming apparatuses such as electrostatic copying machine using a white light source such as halogen lamp, etc., a photosensitive material having sensitivity at the visible range is required. Therefore, for example, the perylene pigment represented by the above general formula (CG3) and bisazo pigment represented by the general formula (CG4) are suitably used.

<Hole Transferring Material>

Examples of the hole transferring material include various compounds having high hole transferring capability, for example, compounds represented by the following general formulas (HT1) to (HT13):

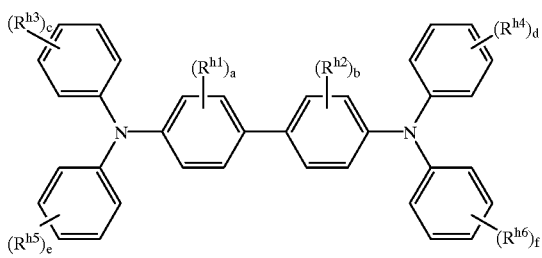

(HT1)

wherein $R^{h1}$, $R^{h2}$, $R^{h3}$, $R^{h4}$, $R^{h5}$ and $R^{h6}$ are the same or different and represent a halogen atom, an alkyl group which may have a substituent, an alkoxy group which may have a substituent, or an aryl group which may have a substituent; a and b are the same or different and represent an integer of 0 to 4; and c, d, e and f are the same or different and represent an integer of 0 to 5; provided that each $R^{h1}$ may be different from one another, when a is 2 or more, and the same is ture for $R^{h2}$, $R^{h3}$, $R^{h4}$, $R^{h5}$ or $R^{h6}$,

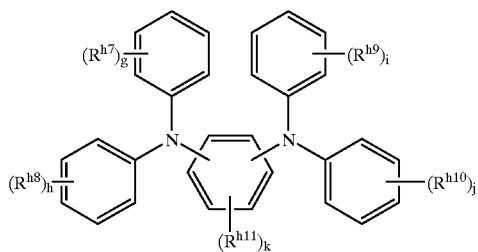

(HT2)

wherein $R^{h7}$, $R^{h8}$, $R^{h9}$, $R^{h10}$ and $R^{h11}$ are the same or different and represent a halogen atom, an alkyl group which may have a substituent, an alkoxy group which may have a substituent, or an aryl group which may have a substituent; g, h, i and j are the same or different and represent an integer of 0 to 5; and k is an integer of 0 to 4; provided that each $R^{h7}$ may be different from one another when g is 2 or more, and the same is true for $R^{h8}$, $R^{h9}$, $R^{h10}$ or $R^{h11}$

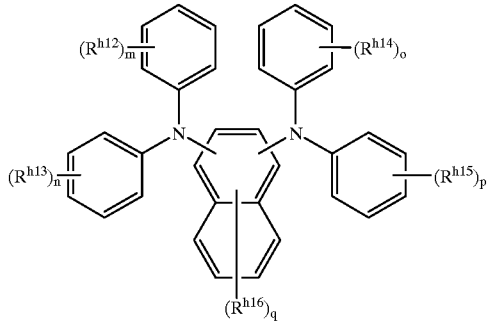

(HT3)

wherein $Rh^{h12}$, $R^{h13}$, $R^{h14}$ and $R^{h15}$ are the same or different and represent a halogen atom, an alkyl group which may have a substituent, an alkoxy group which may have a substituent, or an aryl group which may have a substituent; $R^{h16}$ is a halogen atom, a cyano group, a nitro group, an alkyl group which may have a substituent, an alkoxy group which may have a substituent, or an aryl group which may have a substituent; m, n, o and p are the same or different and represent an integer of 0 to 5; and q is an integer of 1 to 6; provided that each $R^{g12}$ may be different when m is 2 or more, and the same is true for $R^{h13}$, $R^{h14}$, $R^{h15}$ or $R^{h16}$,

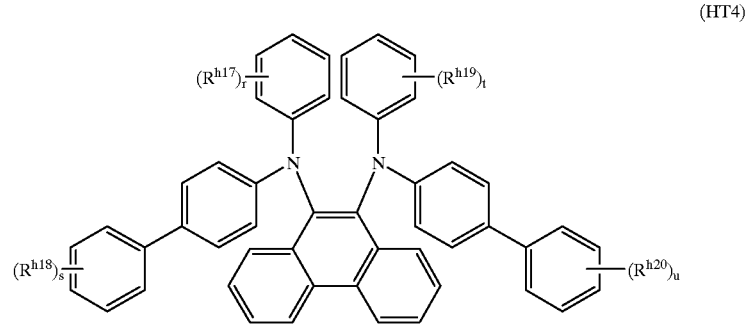

(HT4)

wherein $R^{h17}$, $R^{h18}$, $R^{h19}$ and $R^{h20}$ are the same or different and represent a halogen atom, an alkyl group which may have a substituent, an alkoxy group which may have a substituent, or an aryl group which may have a substituent; r, s, t and u are the same or different and represent an integer of 0 to 5; provided that each $R^{g17}$, $R^{h18}$, $R^{h19}$ and $R^{h20}$ may be different when r, s, t or u is 2 or more,

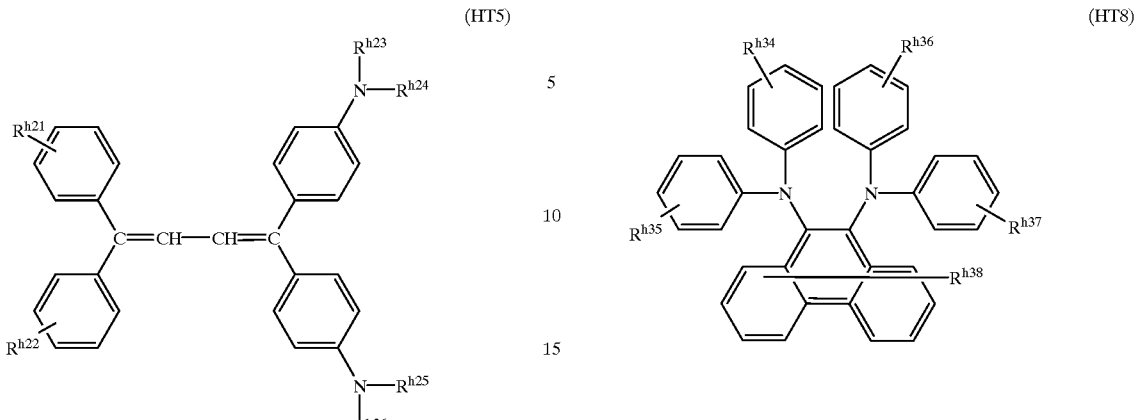

(HT5)

wherein $R^{h21}$ and $R^{h22}$ are the same or different and represent a hydrogen atom, a halogen atom, an alkyl group or an alkoxy group; and $R^{h23}$, $R^{h24}$, $R^{h25}$ and $R^{h26}$ may be same or different and represent a hydrogen atom, an alkyl group or an aryl group,

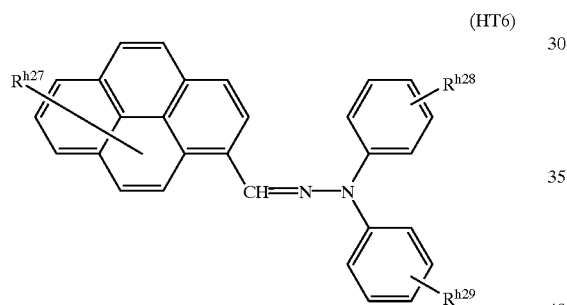

(HT6)

wherein $R^{h27}$, $R^{h28}$ and $R^{h29}$ are the same or different and represent a hydrogen atom, a halogen atom, an alkyl group or an alkoxy group,

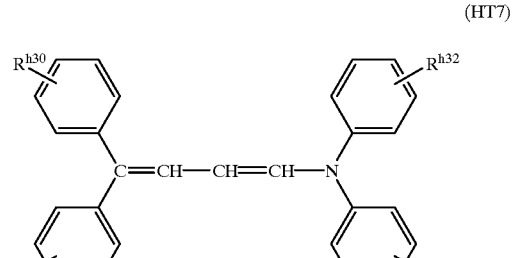

(HT7)

wherein $R^{h30}$, $R^{h31}$, $R^{h32}$ and $R^{h33}$ may be the same or different and represent a hydrogen atom, a halogen atom, an alkyl group or an alkoxy group,

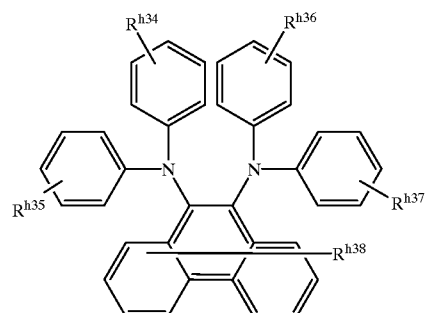

(HT8)

wherein $R^{h34}$, $R^{h35}$, $R^{h36}$, $R^{h37}$ and $R^{h38}$ may be the same or different and represent a hydrogen atom, a halogen atom, an alkyl group or an alkoxy group,

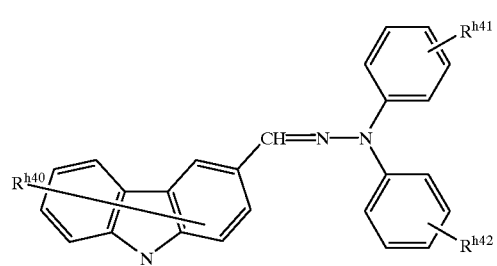

(HT9)

wherein $R^{h39}$ represents a hydrogen atom or an alkyl group; and $R^{h40}$, $R^{h41}$ and $R^{h42}$ may be the same or different and represent a hydrogen atom, a halogen atom, an alkyl group or an alkoxy group,

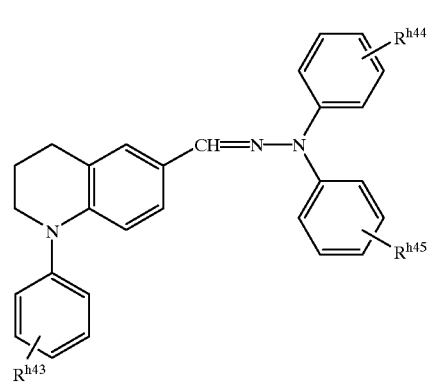

(HT10)

wherein $R^{h43}$, $R^{h44}$ and $R^{h45}$ may be the same or different and represent a hydrogen atom, a halogen atom, an alkyl group or an alkoxy group,

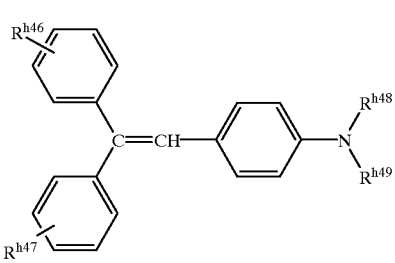

(HT11)

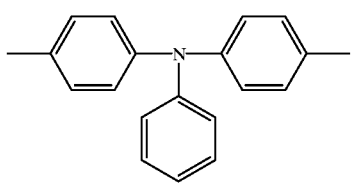

(Φ-1)

wherein $R^{h46}$ and $R^{h47}$ are the same or different and represent a hydrogen atom, a halogen atom, an alkyl group which may have a substituent, or an alkoxy group which may have a substituent; and $R^{h48}$ and $R^{h49}$ are the same or different and represent a hydrogen atom, an alkyl group which may have a substituent, or an aryl group which may have a substituent,

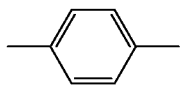

(Φ-2)

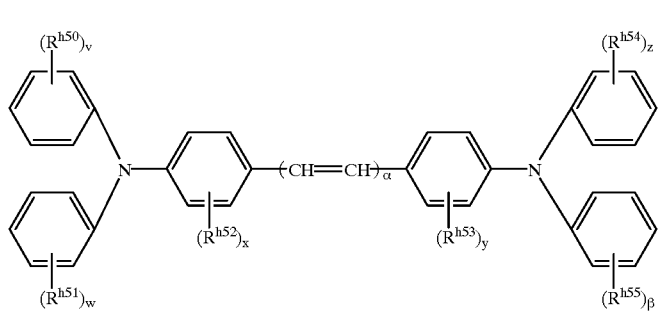

(HT12)

-continued

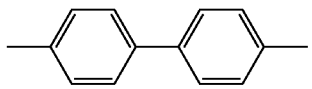

(Φ-3)

wherein $R^{h50}$, $R^{h51}$, $R^{h52}$, $R^{h53}$, $R^{h54}$ and $R^{h55}$ are the same or different and represent an alkyl group which may have a substituent, an alkoxy group which may have a substituent, or an aryl group which may have a substituent; α represents an integer of 1 to 10; v, w, x, y, z and β are the same or different and represent an integer of 0 to 2; provided that each $R^{h50}$ may be different from one another when v is 2, and the same is true for $R^{h51}$, $R^{h52}$, $R^{h53}$, $R^{h54}$ or $R^{h55}$, In the hole transferring material as described above, examples of the alkyl group, alkoxy group and aryl group include the same groups as those described above.

Examples of the substituent which may be substituted on the above groups include halogen atom, amino group, hydroxyl group, optionally esterified carboxyl group, cyano group, alkyl group having 1 to 6 carbon atoms, alkoxy group having 1 to 6 carbon atoms, alkenyl group having 2 to 6 carbon atoms which may have an aryl group, etc. In addition, the substitution positions of the substituents are not specifically limited.

In the present invention, there can be used hole transferring materials which have hitherto been known, that is, nitrogen-containing cyclic compounds and condensed polycyclic compounds, e.g. oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organopolysilane compounds; pyrazoline compounds such as 1-phenyl-3-(p-dimethylaminophenyl)pyrazoline, etc.; hydrazone compounds; triphenylamine compounds; indole compounds; oxazole compounds; isoxazole compounds; thiazole compounds; thiadiazole compounds; imidazole compounds; pyrazole compounds; and triazole compounds.

In the present invention, these hole transferring materials may be used alone or in combination thereof. When using (HT13)

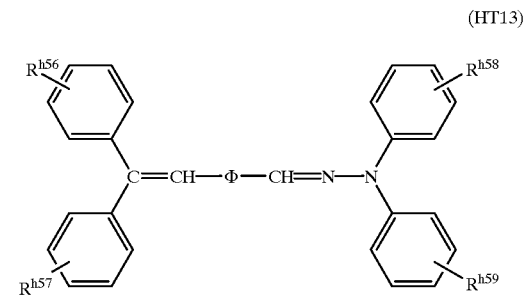

wherein $R^{h56}$, $R^{h57}$, $R^{h58}$ and $R^{h59}$ may be the same or different and represent a hydrogen atom, a halogen atom, an alkyl group or an alkoxy group; and Φ represent any one of groups (Φ-1), (Φ-2) or (Φ-3) respectively represented by the following formulas:

the hole transferring material having film forming properties, such as poly(vinylcarbazole), etc., a resin binder is not required necessarily.

Among the above hole transferring materials, those having an ionization potential (Ip) of from 4.8 to 5.6 eV are preferably used, and those having a mobility of not less than $1\times10^{-6}$ cm$^2$/V.sec. in an electric field strength of $3\times10^5$ V/cm are used, more preferably, in the present invention.

The residual potential is further lowered and the sensitivity is improved by using the hole transferring material having an ionization potential within the above range. The reason is not clear, but is considered as follows.

That is, an easiness of injecting electric charges from the electric charge generating material into the hole transferring material has a close relation with the ionization potential of the hole transferring material. When the ionization potential of the hole transferring material is exceeds the above range, the degree of injection of electric charges from the electric charge generating material into the hole transferring material becomes low, or the degree of the giving and receiving of holes between hole transferring materials becomes low, thereby causing deterioration of the sensitivity. On the other hand, in the system wherein the hole transferring material and electron transferring material coexist, it is necessary to pay attention to an interaction between them, more particularly formation of a charge-transfer complex. When such a complex is formed between them, a recombination arises between holes and electron, which results in deterioration of the mobility of electric charges on the whole. When the ionization potential of the hole transferring material is smaller than the above range, a tendency to form a complex between the hole transferring material and electron transferring material becomes large and a recombination between electrons and holes arises. Consequently, an apparent yield of quantums is decreased, thereby causing deterioration of the photo sensitivity.

When a bulky group exists in the electron transferring material, it is possible to inhibit formation of a charge-transfer complex by a steric hindrance. Accordingly, it is preferable to introduce a substituent which is as bulky as possible into the naphthoquinone derivative (1) used as the electron transferring material in the present invention.

Specific examples of the hole transferring material, which can be suitably used in the present invention, include compounds represented by the formula (HT1-1):

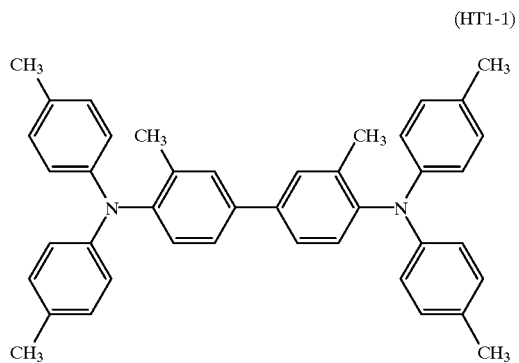

(HT1-1)

which belong to the benzidine derivatives represented by the above general formula (HT1).

<Resin Binder>

As the resin binder for dispersing the above respective components, there can be used various resins which have hitherto been used in the photosensitive layer, and examples thereof include thermoplastic resins such as styrene polymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin, etc.; crosslinking thermosetting resins such as silicone resin, epoxy resin, phenol resin, urea resin, melamine resin, etc.; and photosetting resins such as epoxy acrylate, urethane acrylate, etc. These resin binders can be used alone or in combination thereof. Preferable resin binders are styrene polymer, acrylic polymer, styrene-acrylic copolymer, polyester, alkyd resin, polycarbonate, polyarylate and etc.

In order to obtain a single-layer type electrophotosensitive material, an electric charge generating material, a hole transferring material, a resin binder, and etc. and an electron transferring material may be dissolved or dispersed in a suitable solvent, and the resulting coating solution is applied on a conductive substrate using means such as application, followed by drying.

In the single-layer type photosensitive material, the electric charge generating material is formulated in the amount of 0.1 to 50 parts by weight, preferably 0.5 to 30 parts by weight, based on 100 parts by weight of the resin binder. The electron transferring material is formulated in the amount of 5 to 100 parts by weight, preferably 10 to 80 parts by weight, based on 100 parts by weight of the resin binder. In addition, the hole transferring material is formulated in the amount of 5 to 500 parts by weight, preferably 25 to 200 parts by weight, based on 100 parts by weight of the resin binder. Furthermore, it is suitable that the total amount of the hole transferring material and electron transferring material is 10 to 500 parts by weight, preferably 30 to 200 parts by weight, based on 100 parts by weight of the resin binder. When the electron acceptive compound is contained, the amount is 0.1 to 40 parts by weight, preferably 0.5 to 20 parts by weight, based on 100 parts by weight of the resin binder.

The thickness of the single-layer type photosensitive material is 5 to 100 μm, preferably 10 to 50 μm.

In order to obtain the multi-layer type electrophotosensitive material, an electric charge generating layer containing an electric charge generating material may be formed on a conductive substrate using means such as deposition, application, etc., and then a coating solution containing an electron transferring material and a resin binder is applied on the electric charge generating layer using means such as application, followed by drying, to form an electric charge-transferring layer.

In the multi-layer photosensitive material, the electric charge generating material and resin binder which constitute the electric charge generating layer may be used in various proportions. It is suitable that the electric charge generating material is formulated in the amount of 5 to 1000 parts by weight, preferably 30 to 500 parts by weight, based on 100 parts by weight of the resin binder. When an electron acceptive compound is contained in the electric charge generating layer, it is suitable that the electron acceptive compound is formulated in the amount of 0.1 to 40 parts by weight, preferably 0.5 to 20 parts by weight, based on 100 parts by weight of the resin binder. In addition, when an electron transferring material is contained in the electric charge generating layer, it is suitable that the electron transferring material is formulated in the amount of 0.5 to 50 parts by weight, preferably 1 to 40 parts by weight, based on 100 parts by weight of the resin binder.

The electron transferring material and resin binder, which constitute the electric charge-transferring layer, can be used in various proportions within such a range as not to prevent the transfer of electrons and to prevent the crystallization. It is suitable that the electron transferring material is used in the amount of 10 to 500 parts by weight, preferably 25 to 100 parts by weight, based on 100 parts by weight of the resin binder so as to easily transfer electrons generated by light irradiation in the electric charge generating layer. When an electron acceptive compound is contained in the electric charge transferring layer, it is suitable that the electron acceptive compound is formulated in the amount of 0.1 to 40 parts by weight, preferably 0.5 to 20 parts by weight, based on 100 parts by weight of the resin binder.

Regarding the thickness of the multi-layer type photosensitive layer, the thickness of the electric charge generating layer is about 0.01 to 5 $\mu$m, preferably about 0.1 to 3 $\mu$m, and that of the electric charge-transferring layer is 2 to 100 $\mu$m, preferably about 5 to 50 $\mu$m.

A barrier layer may be formed, in such a range as not to injure the characteristics of the photosensitive material, between the conductive substrate and photosensitive layer in the single-layer type photosensitive material, or between the conductive substrate and electric charge generating layer or between the conductive substrate layer and electric charge-transferring layer in the multi-layer type photosensitive material. Further, a protective layer may be formed on the surface of the photosensitive layer.

In addition, various additives which have hitherto been known, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors, etc. can be formulated in the single-layer type or multi-layer type photosensitive layer without injury to the electrophotographic characteristics. In order to improve the sensitivity of the photosensitive layer, known sensitizers such as terphenyl, halonaphthoquinones, acenaphthylene, etc. may be used in combination with the electric charge generating material.

Furthermore, various electron transferring materials having high electron transferring capability may be contained in the photosensitive layer, together with the naphthoquinone derivative represented by the above general formula (1).

As the conductive substrate to be used in the electrophotosensitive material of the present invention, various materials having the conductivity can be used, and examples thereof include single metals such as aluminum, iron, copper, tin, platinum, silver, vanadium, molybdenum, chromium, cadmium, titanium, nickel, palladium, indium, stainless steel, brass, etc.; plastic materials which are vapor-deposited or laminated with the above metal; glass materials coated with aluminum iodide, tin oxide, indium oxide, etc.

The conductive substrate may be made in the form of a sheet or a drum. The substrate itself may have a conductivity or only the surface of the substrate may have a conductivity. It is preferred that the conductive substrate has sufficient mechanical strength when used.

The photosensitive layer in the electrophotosensitive material of the present invention is produced by applying a coating solution, obtained by dissolving or dispersing a resin composition containing the above respective components in a suitable solvent, on a conductive substrate, followed by drying.

That is, the above electric charge generating material, electric charge-transferring material and resin binder may be dispersed and mixed with a suitable solvent by a known method, for example, using a roll mill, a ball mill, an atriter, a paint shaker, a supersonic dispenser, etc. to prepare a dispersion, which is applied by a known means and then allowed to dry.

As the solvent for preparing the coating solution, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; halogenated hydrocarbons such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethyl sulfoxide, etc. These solvents may be used alone or in combination thereof.

In order to improve a dispersibility of the electric charge-transferring material and electric charge generating material as well as a smoothness of the surface of the photosensitive layer, there may be used surfactants, leveling agents, etc.

EXAMPLES

The following Synthesis Examples and Examples further illustrate the present invention in detail.

Synthesis Example 1

[Synthesis of 1,4-benzenedimethanol,bis(3-phenyl-1,4-naphthoquinone-2-carboxylate) represented by the above general formula (1-1)]

In a two neck flask, 1,4-benzenedimethanol (108 mmol, 14.9 g), bromoacetic acid (216 mmol, 30 g) and 200 ml of toluene were added, and then several drops of concentrated sulfuric acid were added to the toluene solution. After a Dean-stark device was mounted to the two neck flask, the mixture was stirred under reflux for about 6 hours. After the completion of the reaction, the solution was cooled to room temperature. Water was added and then the reaction solution was extracted with ethyl acetate. The obtained ethyl acetate layer was dried over sodium sulfate and the solvent was evaporated under reduced pressure to obtain colorless transparent 1,4-benzenedimethanol, dibromoacetate (yield 64%, 40 g).

In a four neck flask to which a reflux tube is connected, 2-phenyl-1,3-indandione (0.2 mmol, 45 g) of the above formula (6) in which $R^1$ is a phenyl group and sodium hydride (0.23 mol, 9 g) were added and, after the flask was sufficiently deaerated, dried and then replaced by an argon gas, 250 ml of anhydrous tetrahydrofuran was added while ice cooling the flask vessel.

After stirring until generation of hydrogen from the solution stopped, 1,4-benzenedimethanol, dibromscetate (0.17 mmol, 40 g) was added and solution was reacted by stirring under reflux for 4 hours. After the completion of the reaction, aqueous hydrochloric acid was added to the solution. The reaction solution was extracted with chloroform and the obtained chloroform layer was dried over anhydrous sodium sulfate. After the solvent was evaporated under reduced pressure, the resulting residue was precipitated in a tetrahydrofuran/hexane mixed solution to obtain 1,4-benzenedimethanol, bis(1,3-diketo-2-phenylindene)acetate (yield 68%, 45 g).

In a round-bottom flask to which a reflux condenser is connected, the above 1,4-benzenedimethanol,bis(1,3-diketo-2-phenylindene) acetate and sodium hydride (35 mmol, 1.5 g) were added and, after the flask was sufficiently deaerated, dried and then replaced by an argon gas, 150 ml of anhydrous tetrahydrofuran was added while ice cooling the flask. The tetrahydrofuran solution was reacted by stirring under reflux for 6 hours. After the completion of the reaction, hydrochloric acid was added to the solution and the reaction solution was extracted with chloroform. The obtained chloroform layer was dried over anhydrous sodium sulfate. Then, tetrachlorobenzoquinone(chloranil) (30 mmol, 8 g) was added to the solution, followed by stirring at room temperature overnight. After the completion of the reaction, the solid in the solution was filtered and the filtrate was evaporated under reduced pressure to deposit the solid. Then, the solid was recrystallized from ethanol to obtain the titled compound (yield 30%, 3 g, melting point: 156–158° C.).

Figure 2:
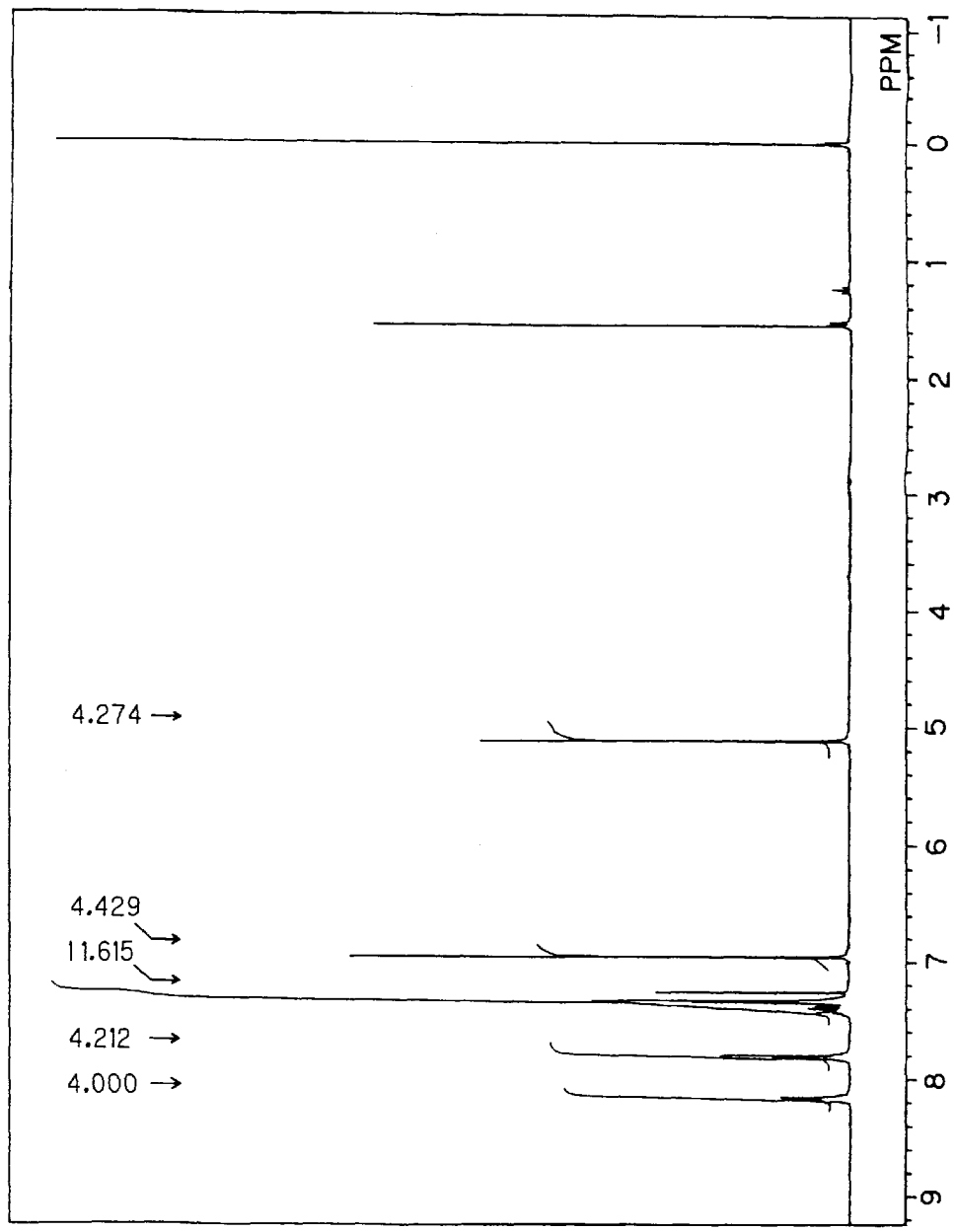
FIG. 2 to FIG. 5 are graphs illustrating each $^1$H-NMR spectrum of naphthoquinone derivatives (1-1) to (1–4) obtained in the respective Synthetic Examples.

The $^1$H-NMR spectrum of the product is shown in FIG. 2.

Synthesis Example 2
[Synthesis of ethylene glycol, bis(3-phenyl-1,4-naphthoquinone-2-carboxylate) represented by the above general formula (1-2)]

According to the same manner as that described in Synthesis Example 1 except for using the same molar amount of ethylene glycol of the above general formula (8) in which $R^2$ is an ethyl group, the reaction was performed to obtain the titled compound (yield 36%, melting point: 228–231° C.).

Figure 3:
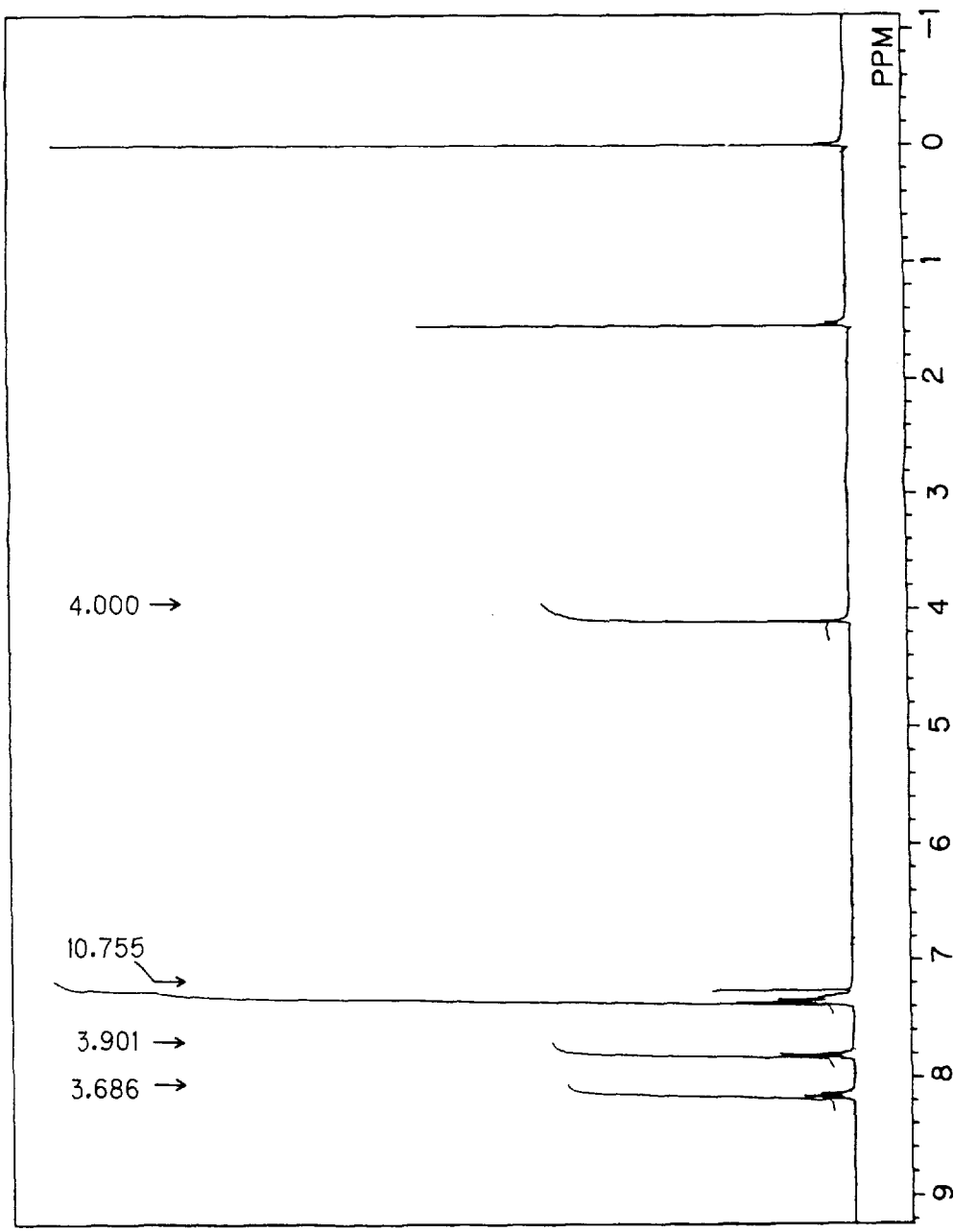

The $^1$H-NMR spectrum of the product is shown in FIG. 3.

Synthesis Example 3
[Synthesis of resorcinol, bis(3-phenyl-1,4-naphthoquinone-2-carboxylate) represented by the above general formula (1-3)]

According to the same manner as that described in Synthesis Example 1 except for using the same molar amount of resorcinol of the above general formula (8) in which $R^2$ is a 1,3-phenyl group, the reaction was performed to obtain the titled compound (yield 20%, melting point: 181–183° C.).

Figure 4:
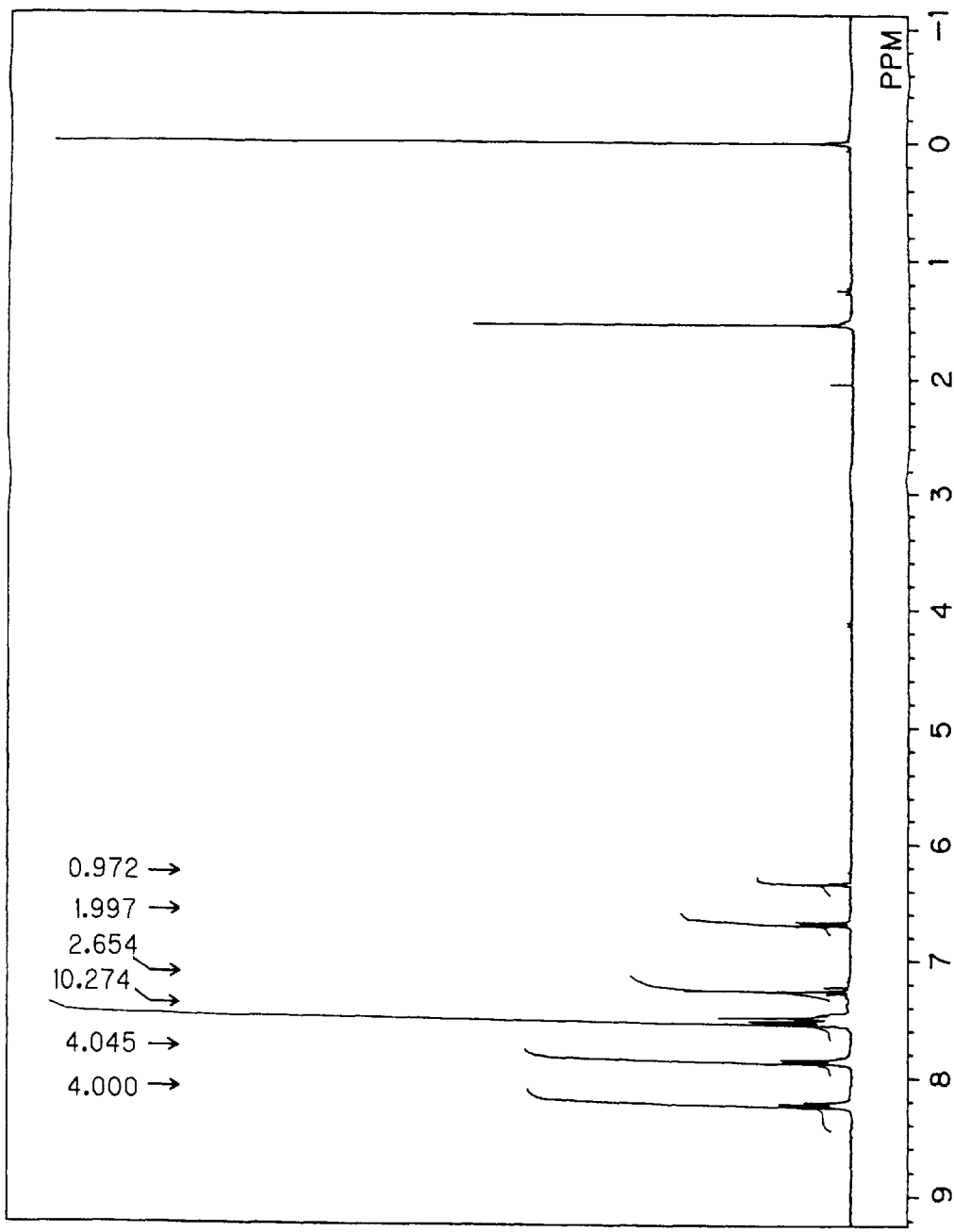

The $^1$H-NMR spectrum of the product is shown in FIG. 4.

Synthesis Example 4
[Synthesis of 4,4'-di(3-phenyl-1,4-naphthoquinone-2-carbonyloxy)diphenyl ether represented by the above general formula (1-4)]

According to the same manner as that described in Synthesis Example 1 except for using the same molar amount of 4,4'-dihydroxydiphenyl ether of the above general formula (8) in which $R^2$ is a 4,4'-diphenyl ether group, the reaction was performed to obtain the titled compound (yield 25%, melting point: 175–177° C.).

Figure 5:
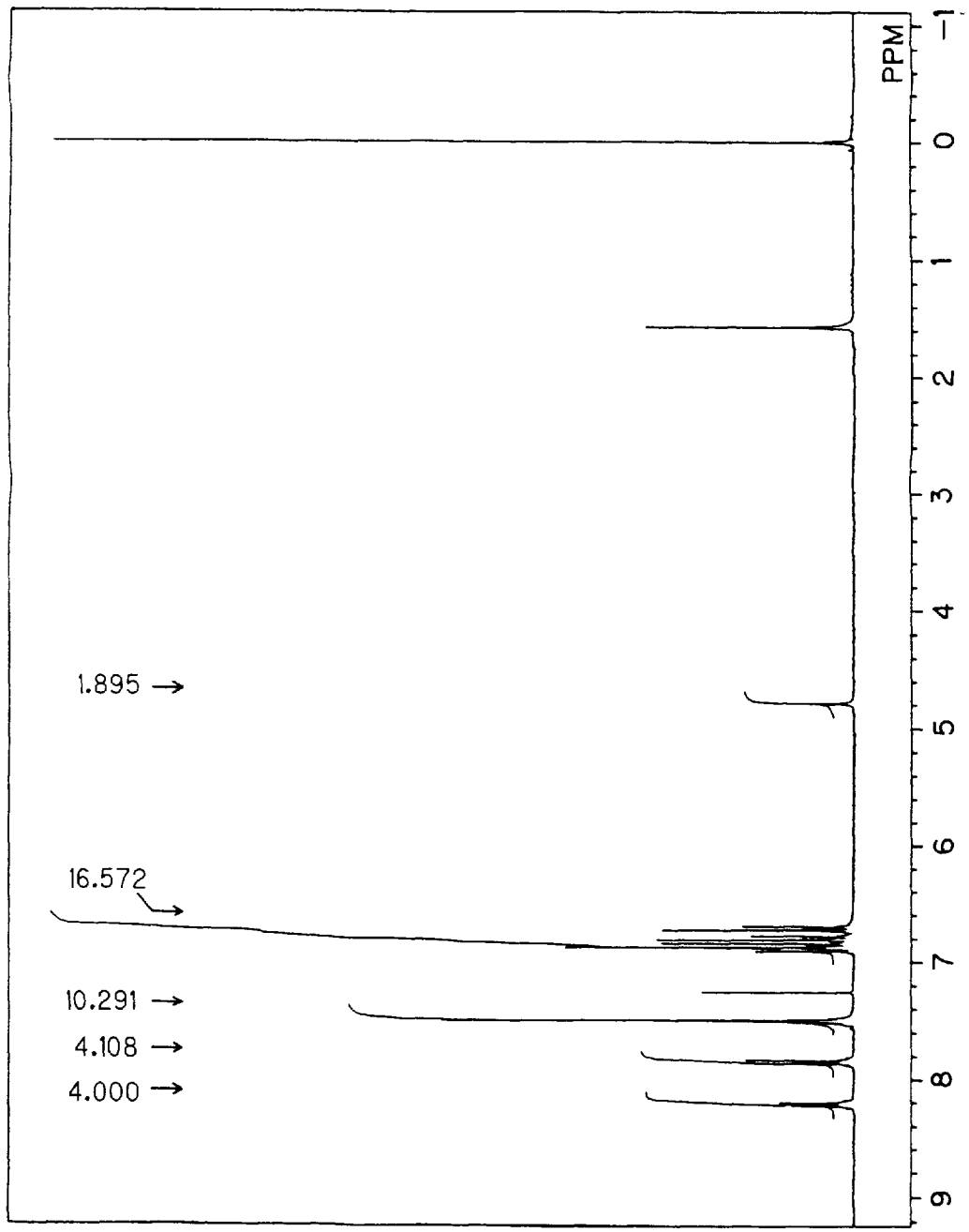

The $^1$H-NMR spectrum of the product is shown in FIG. 5.

[Production of Electrophotosensitive Material]

The respective components used in the electrophotosensitive material of the present invention are as follows.

(i) Electric Charge Generating Material

PcH$_2$: X-type metal-free phthalocyanine represented by the above formula (CG1) [ionization potential (Ip) =5.38 eV]

PcTiO: oxotitanyl phthalocyanine represented by the above formula (CG2) [Ip=5.32 eV]

Perylene: perylene pigment (Ip=5.50 eV) represented by the following formula (CG3-1):

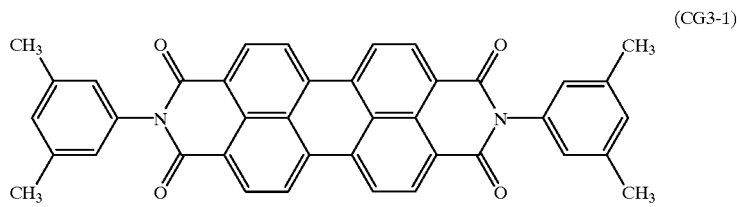

(CG3-1)

which belongs to the above general formula (CG3)

(ii) Hole Transferring Material

HT1-1: benzidine derivative (Ip=5.56 eV) represented by the above formula (HT1-1)

(iii) Electron Transferring Material 1-1: naphthoquinone derivative represented by the above formula (1-1)

1-2: naphthoquinone derivative represented by the above formula (1-2)

1-3: naphthoquinone derivative represented by the above formula (1-3)

1-4: naphthoquinone derivative represented by the above formula (1-4)

ET13-1: 3-phenyl-1,4-naphthoquinone represented by the following formula (ET13-1):

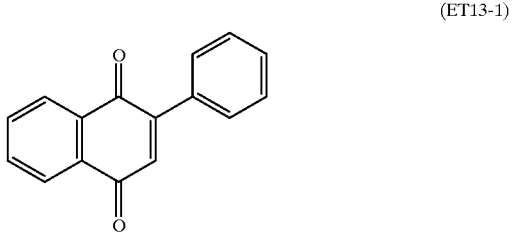

(ET13-1)

which belongs to the naphthoquinone derivative represented by the above formula (ET13) disclosed in Japanese Patent Laid-Open Publication No. 6-110227

3-1: p-benzoquinone (redox potential=−0.81 V) represented by the above formula (3-1)

3-2: 2,6-di-t-butyl-p-benzoquinone (redox potential =−1.30 V) represented by the above formula (3-2)

2-1: 3,5-dimethyl-3',5'-di-t-butyl-4,4'-diphenoquinone (redox potential=−0.86 V) represented by the above formula (2-1)

2-2: 3,3',5,5'-tetra-t-butyl-4,4'-diphenoquinone (redox potential=−0.94 V) represented by the above formula (2-2)

The above ionization potential was measured under atmospheric pressure using a photoelectric analyzer (AC-1, manufactured by Riken Keiki Co., Ltd.).

[Production of Single-Layer Type Electrophotosensitive Material]

EXAMPLES 1 TO 12 AND COMPARATIVE EXAMPLES 1 to 8

An electric charge generating material, a hole transferring material, an electron transferring material, a resin binder and a solvent were formulated in the proportion shown below, and then mixed and dispersed in a ball mill for 50 hours to prepare a coating solution for single-layer type photosensitive layer.

| (Components) | (Parts by weight) |
|---|---|
| Electric charge generating material | 5 |
| Hole transferring material | 50 |
| Electron transferring material | 30 |
| Resin binder (polycarbonate) | 100 |
| Solvent (tetrahydrofuran) | 800 |

Then, the above coating solution was applied on an aluminum tube by depcoating method, followed by hot-air drying at 100° C. for 60 minutes to obtain a single-layer type electrophotosensitive material of 15 to 20 μm in film thickness, respectively.

EXAMPLES 21 TO 36 AND COMPARATIVE EXAMPLES 13 TO 16

According to the same manner as that described in Examples 1 to 3 except for preparing a coating solution for single-layer type photosensitive layer by further formulating 10 parts by weight of each of electron transferring materials represented by the above formula (2-1) to (2-2) and (3-1) to (3-2) having an predetermined redox potential, in addition to 5 parts by weight of an electric charge generating material, 50 parts by weight of a hole transferring material, 30 parts by weight of an electron transferring material, 100 parts by weight of a resin binder and 800 parts by weight of a solvent shown in Table 2 and Table 3, a single-layer type electrophotosensitive material was produced, respectively.

[Production of Multi-Layer Type Electrophotosensitive Material]

EXAMPLES 13 TO 20 AND COMPARATIVE EXAMPLES 9 To 12

100 Parts by weight of an electric charge generating material, 100 parts by weight of a resin binder (polyvinyl butyral) and 2000 parts by weight of a solvent (tetrahydrofuran) were mixed and dispersed in a ball mill for 50 hours to prepare a coating solution for electric charge generating layer. Then, this coating solution was applied on an aluminum tube as the conductive substrate by a dip coating method, followed by hot-air drying at 100° C. for 60 minutes to form an electric charge generating layer of 1 μm in film thickness.

On the other hand, 100 parts by weight of an electron transferring material, 100 parts by weight of a resin binder (polycarbonate) and 800 parts by weight of a solvent (toluene) shown in Table 1 to Table 3 were mixed and dispersed in a ball mill for 50 hours to prepare a coating solution for electric charge-transferring layer. Then, this coating solution was applied on the above electric charge generating layer, followed by hot-air drying at 100° C. for 60 minutes to form an electric charge-transferring layer of 20 μm in film thickness, thereby producing a multi-layer type electrophotosensitive material, respectively.

(Evaluation of Characteristics of Photosensitive Material)

The electrophotosensitive materials obtained in the above Examples and Comparative Examples were subjected to the following photosensitivity test, and their sensitivity characteristics were evaluated.

Photosensitivity Test

By using a drum sensitivity tester manufactured by GENTEC Co., a voltage was applied on the surface of the photosensitive material of the above respective Examples and Comparative Examples to charge the surface at +700 V. Then, this photosensitive material was exposed by irradiating light to measure a potential $V_L$ (V) of the surface of the photosensitive material at the time at which 330 msec. has passed since the beginning of exposure.

Further, the condition of light irradiation varies depending on the kind of the electric charge generating material (i.e. phthalocyanine pigment, perylene pigment, etc.) as shown below.

(1) In Case of Phthalocyanine Pigment

Monochromic light having a wavelength of 780 nm (half-width: 20 nm) and a light intensity of 16 μW/cm$^2$ from a halogen lamp through a band-pass filter was irradiated on the surface of the photosensitive material charged at +700 V for 80 msec.

(2) In Case of Perylene Pigment

White light (light intensity: 147 μW/cm$^2$) of a halogen lamp was irradiated on the surface of the photosensitive material charged at +700 V for 50 msec.

The components used in the above Examples and Comparative Examples as well as measuring results of the potential after exposure $V_L$ are shown in Tables 1 to 3.

<Tables 1 to 3>

TABLE 1

| | electric charge generating material | hole transferring material | electron transferring material | $V_L$ (V) |
|---|---|---|---|---|
| Example 1 | PcH$_2$ | HT1-1 | 1-1, — | 196 |
| Example 2 | PcTio | HT1-1 | 1-1, — | 211 |
| Example 3 | Perylene | HT1-1 | 1-1, — | 234 |
| Example 4 | PcH$_2$ | HT1-1 | 1-2, — | 198 |
| Example 5 | PcTio | HT1-1 | 1-2, — | 214 |
| Example 6 | Perylene | HT1-1 | 1-2, — | 236 |
| Example 7 | PcH$_2$ | HT1-1 | 1-3, — | 194 |
| Example 8 | PcTio | HT1-1 | 1-3, — | 209 |
| Example 9 | Perylene | HT1-1 | 1-3, — | 233 |
| Example 10 | PcH$_2$ | HT1-1 | 1-4, — | 193 |
| Example 11 | PcTio | HT1-1 | 1-4, — | 208 |
| Example 12 | Perylene | HT1-1 | 1-4, — | 232 |
| Example 13 | PcH$_2$ | — | 1-1, — | 303 |
| Example 14 | Perylene | — | 1-1, — | 316 |
| Example 15 | PcH$_2$ | — | 1-2, — | 305 |
| Example 16 | Perylene | — | 1-2, — | 319 |
| Example 17 | PcH$_2$ | — | 1-3, — | 301 |
| Example 18 | Perylene | — | 1-3, — | 314 |
| Example 19 | PcH$_2$ | — | 1-4, — | 300 |
| Example 20 | Perylene | — | 1-4, — | 314 |

TABLE 2

| | electric charge generating material | hole transferring material | electron transferring material | $V_L$ (V) |
|---|---|---|---|---|
| Example 21 | PcH$_2$ | HT1-1 | 1-1, 3-1 | 162 |
| Example 21 | PcH$_2$ | HT1-1 | 1-1, 3-1 | 162 |
| Example 22 | PcH$_2$ | HT1-1 | 1-1, 3-2 | 158 |
| Example 23 | PcH$_2$ | HT1-1 | 1-1, 2-1 | 157 |
| Example 24 | PcH$_2$ | HT1-1 | 1-1, 2-2 | 151 |
| Example 25 | PcH$_2$ | HT1-1 | 1-2, 3-1 | 166 |
| Example 26 | PcH$_2$ | HT1-1 | 1-2, 3-2 | 161 |
| Example 27 | PcH$_2$ | HT1-1 | 1-2, 2-1 | 160 |
| Example 28 | PcH$_2$ | HT1-1 | 1-2, 2-2 | 153 |

TABLE 2-continued

| | electric charge generating material | hole transferring material | electron transferring material | $V_L$ (V) |
|---|---|---|---|---|
| Example 29 | $PcH_2$ | HT1-1 | 1-3, 3-1 | 160 |
| Example 30 | $PcH_2$ | HT1-1 | 1-3, 3-2 | 156 |
| Example 31 | $PcH_2$ | HT1-1 | 1-3, 2-1 | 155 |
| Example 32 | $PcH_2$ | HT1-1 | 1-3, 2-2 | 150 |
| Example 33 | $PcH_2$ | HT1-1 | 1-4, 3-1 | 160 |
| Example 34 | $PcH_2$ | HT1-1 | 1-4, 3-2 | 155 |
| Example 35 | $PcH_2$ | HT1-1 | 1-4, 2-1 | 153 |
| Example 36 | $PcH_2$ | HT1-1 | 1-4, 2-2 | 148 |

TABLE 3

| | electric charge generating material | hole transferring material | electron transferring material | $V_L$ (V) |
|---|---|---|---|---|
| Comparative Example 1 | $PcH_2$ | HT1-1 | ET13-1, — | 305 |
| Comparative Example 2 | PcTio | HT1-1 | ET13-1, — | 330 |
| Comparative Example 3 | Perylene | HT1-1 | ET13-1, — | 375 |
| Comparative Example 4 | $PcH_2$ | HT1-1 | 2-1, — | 220 |
| Comparative Example 5 | PcTio | HT1-1 | 2-1, — | 242 |
| Comparative Example 6 | $PcH_2$ | HT1-1 | —, — | 478 |
| Comparative Example 7 | Perylene | HT1-1 | 2-1, — | 294 |
| Comparative Example 8 | Perylene | HT1-1 | —, — | 521 |
| Comparative Example 9 | $PcH_2$ | — | ET13-1, — | 409 |
| Comparative Example 10 | Perylene | — | ET13-1, — | 455 |
| Comparative Example 11 | $PcH_2$ | — | 2-1, — | 346 |
| Comparative Example 12 | Perylene | — | 2-1, — | 386 |
| Comparative Example 13 | $PcH_2$ | HT1-1 | ET13-1, 3-1 | 295 |
| Comparative Example 14 | $PcH_2$ | HT1-1 | ET13-1, 3-2 | 290 |
| Comparative Example 15 | $PcH_2$ | HT1-1 | ET13-1, 2-1 | 290 |
| Comparative Example 16 | $PcH_2$ | HT1-1 | ET13-1, 2-2 | 288 |

As is apparent from Tables 1 to 3, the photosensitive materials of the examples have high sensitivity because their potential after exposure are reduced in comparison with the photosensitive material using a conventional electron transferring material or using no electron transferring material of the Comparative Examples.

It is apparent that the photosensitive materials of Examples 21 to 36 have high sensitivity because they contain the electron transferring material having a predetermined redox potential and naphthoquinone derivative (1) of the present invention and their potentials after exposure are reduced in comparison with the photosensitive materials of other Examples.

What is claimed is:

1. A naphthoquinone derivative represented by the general formula (1):

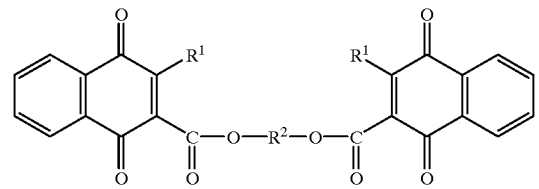

wherein $R^1$ represents an aryl group which may have a substituent; and $R^2$ represents an alkylene group which may have a substituent, an arylene group which may have a substituent, a group (i):

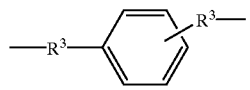

($R^3$ represents an alkylene group which may have a substituent), or a group (ii)

2. The naphthoquinone derivative defined in claim 1, represented by the general formula (11):

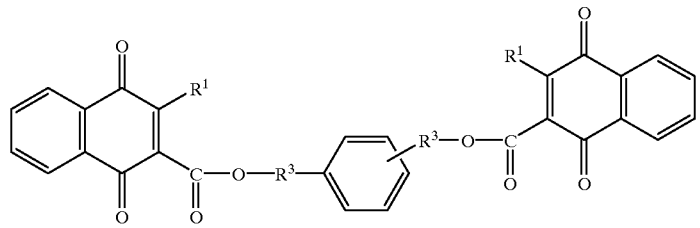

wherein $R^1$ represents an aryl group which may have a substituent and $R^3$ represents an alkylene group which may have a substituent.

3. The naphthoquinone derivative defined in claim 1, represented by the general formula (12):

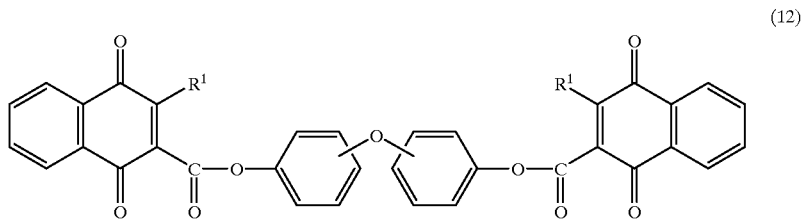

(12)

wherein $R^1$ represents an aryl group which may have a substituent.

4. The naphthoquinone derivative defined in claim 1, represented by the general formula (13):

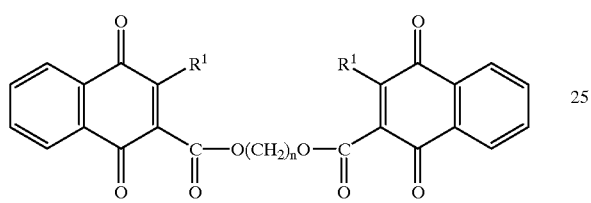

(13)

wherein $R^1$ represents an aryl group which may have a substituent and n represents an integer of 1 to 6.

5. The naphthoquinone derivative defined in claim 1, represented by the general formula (14):

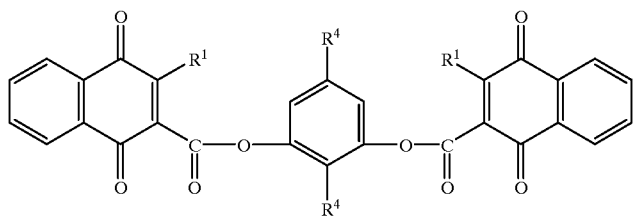

(14)

wherein $R^1$ represents an aryl group which may have a substituent and $R^4$ represents a hydrogen atom, an alkyl group or a halogen atom.

* * * * *